United States Patent [19]

Rosen

[11] Patent Number: 5,686,615

[45] Date of Patent: Nov. 11, 1997

[54] STEREOSELECTIVE PREPARATION OF SUBSTITUTED PIPERIDINES

[75] Inventor: Terry J. Rosen, East Lyme, Conn.

[73] Assignee: Pfizer Inc, New York, N.Y.

[21] Appl. No.: 119,149

[22] Filed: Sep. 20, 1993

Related U.S. Application Data

[63] Continuation-in-part of Ser. No. 675,244, Mar. 26, 1991, abandoned.

[51] Int. Cl.$^6$ .................................................. C07D 211/32
[52] U.S. Cl. ................................................ 546/185
[58] Field of Search ............................. 546/223, 192, 546/193, 205, 206, 201, 207, 208, 212, 214, 213, 185

[56] References Cited

U.S. PATENT DOCUMENTS

| | | | |
|---|---|---|---|
| 2,355,659 | 8/1944 | Nutley et al. | 546/185 X |
| 4,267,318 | 5/1981 | Hershenson | 542/422 |

FOREIGN PATENT DOCUMENTS

| | | | |
|---|---|---|---|
| 436334 | 7/1991 | European Pat. Off. | 546/185 |
| 9118878 | 12/1991 | WIPO . | |

OTHER PUBLICATIONS

H. Rodd. *Rodd's Chemistry of Carbon Compounds*, Elsevier Scientific Publishing Co., pp. 212–213 (1976).

H. House, *Modern Synthetic Reactions*, Second Edition, W. A. Benjamin, Inc., pp. 3–15 (1972).

Solomons, T W Graham *Organic Chemistry* (1988) pp. 259–264.

*Primary Examiner*—James H. Reamer
*Attorney, Agent, or Firm*—P. C. Richardson; P. H. Ginsburg; G. Butterfield

[57] ABSTRACT

Novel processes are disclosed for the stereoselective preparation of substituted piperidine derivatives of the formulae

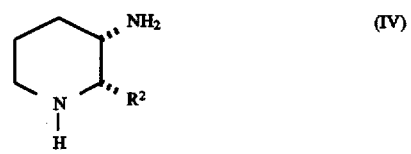

and

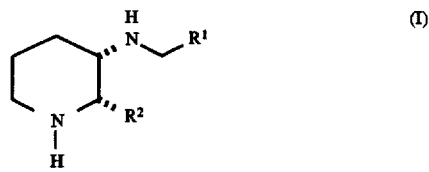

wherein $R^1$ and $R^2$ are defined as below, useful as substance P receptor antagonists and in treating diseases mediated by an excess of substance P.

30 Claims, No Drawings

STEREOSELECTIVE PREPARATION OF SUBSTITUTED PIPERIDINES

This is the national stage application of PCT application PCT/US92/00065, filed Jan. 14, 1992, which published as WO 92/17449 on Oct. 15, 1992, and was a continuation-in-part application of U.S. patent application Ser. No. 07/675,244, filed Mar. 26, 1991, now abandoned.

BACKGROUND OF THE INVENTION

This invention relates to novel processes for the stereoselective preparation of substituted piperidine derivatives.

The substituted piperidines and related compounds that can be prepared by the processes of this invention are substance P receptor antagonists and are therefore useful in treating diseases mediated by an excess of substance P.

Substance P is a naturally occurring undecapeptide belonging to the tachykinin family of peptides, the latter being named for their prompt stimulatory action on smooth muscle tissue. More specifically, substance P is a pharmacologically-active neuropeptide that is produced in mammals (having originally been isolated from gut) and possesses a characteristic amino acid sequence that is illustrated by D. F. Veber et al. in U.S. Pat. No. 4,680,283.

The wide involvement of substance P and other tachykinins in the pathophysiology of numerous diseases has been amply demonstrated in the art. For instance, substance P has been shown to be involved in the transmission of pain or migraine (see B. E. B. Sandberg et al., *Journal of Medicinal Chemistry*, Vol. 25, p. 1009 (1982)), as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract, such as ulcerative colitis and Crohn's disease, etc. (see D. Regoli in "Trends in Cluster Headache," edited by F. Sicuteri et al., Elsevier Scientific Publishers, Amsterdam, 1987, pp. 85–95).

Several of the substituted piperidines and related compounds that can be prepared by the methods of this invention are claimed in PCT Patent Application PCT/US 90/00116, filed Jan. 4, 1990, U.S. patent application Ser. No. 07/717,943, filed Jun. 20, 1991 and U.S. patent application Ser. No. 07/724,268, entitled "3-Aminopiperidine Derivatives and Related Nitrogen Containing Hetercycles" and filed Jul. 1, 1991, all of which are assigned in common with the present application. Other methods for preparing such compounds referred to in the United State Patent Application entitled "Preparation of Substituted Piperidines", which was filed in Nov. 27, 1991 and is assigned in common with the present application.

SUMMARY OF THE INVENTION

The present invention relates to a process for preparing a compound of the formula

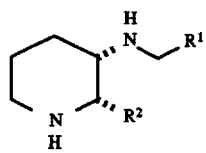

(I)

wherein $R^1$ is aryl selected from indanyl, phenyl and naphthyl; heteroaryl selected from thienyl, furyl, pyridyl and quinolyl; and cycloalkyl having 3 to 7 carbon atoms, wherein one of said carbon atoms may optionally be replaced by nitrogen, oxygen or sulfur; wherein each of said aryl and heteroaryl groups may optionally be substituted with one or more substituents, and said $(C_3-C_7)$cycloalkyl may optionally be substituted with one or two substituents, said substituents being independently selected from chloro, fluoro, bromo, iodo, nitro, $(C_1-C_{10})$alkyl optionally substituted from one to three fluoro groups, $(C_1-C_{10})$alkoxy optionally substituted with from one to three fluoro groups, amino, $(C_1-C_{10})$alkyl-S—,

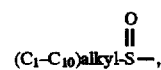

$(C_1-C_{10})$alkyl-$SO_2$—, phenyl, phenoxy, $(C_1-C_{10})$alkyl-$SO_2$NH—, $(C_1-C_{10})$alkyl-$SO_2$NH—$(C_1-C_{10})$alkyl-, $(C_1-C_{10})$alkylamino-di$(C_1-C_{10})$alkyl-, cyano, hydroxy, cycloalkoxy having 3 to 7 carbon atoms, $(C_1-C_6)$alkylamino, $(C_1-C_6)$dialkylamino,

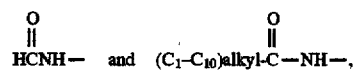

wherein the nitrogen atoms of said amino and $(C_1-C_6)$alkylamino groups may optionally be protected with an appropriate protecting group; and $R^2$ is thienyl, benzhydryl, naphthyl or phenyl optionally substituted with from one to three substituents independently selected from chloro, bromo, fluoro, iodo, cycloalkoxy having 3 to 7 carbon atoms, $(C_1-C_{10})$alkyl optionally substituted with from one to three fluoro groups and $(C_1-C_{10})$alkoxy optionally substituted with from one to three fluoro groups, comprising reacting a compound of the formula

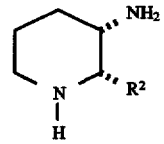

(IV)

wherein $R^2$ is defined as above, with either (a) a compound of the formula

wherein $R^1$ is defined as above and X is a leaving group (e.g., chloro, bromo, iodo or imidazole), followed by treatment of the resulting amide with a reducing agent, (b) a compound of the formula $R^1CHO$, wherein $R^1$ is defined as above, in the presence of a reducing agent, or (c) a compound of the formula $R^1CH_2X$, wherein $R^1$ is defined as above and X is a leaving group (e.g., chloro, bromo, iodo, mesylate or tosylate).

As used herein, the term "halo" refers to chloro, bromo, fluoro or iodo.

The compounds of formula I have chiral centers and therefore exist in different enantiomeric forms. Formula I, as depicted above, includes all optical isomers of such compounds, and mixtures thereof.

The present invention also relates to a process for preparing a compound of the formula I, as depicted above, wherein $R^1$ and $R^2$ are defined as above, comprising reacting a compound of the formula IV, as depicted above, wherein $R^2$ is defined as above, with a compound of the formula $R^1CHO$, wherein $R^1$ is defined above, in the presence of a drying agent or using an apparatus designed to remove azeotropically the water generated, to produce an imine of the formula

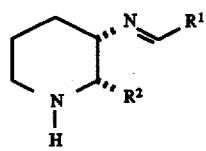

wherein $R^1$ and $R^2$ are defined as above, and then reacting the imine with a reducing agent to form a compound of the formula I, as depicted above, wherein $R^1$ and $R^2$ are defined as above.

The present invention also relates to a process for preparing a compound of the formula I, as depicted above, wherein $R^1$ and $R^2$ are defined as above, comprising reducing a compound of the formula

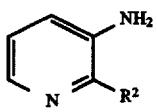

(II)

wherein $R^2$ is defined as above, to produce a compound of the formula IV, as depicted above, wherein $R^2$ is defined as above, and then converting the compound of formula IV so formed to a compound of the formula I using one of the procedures described above.

This invention also relates to a process for preparing a compound of the formula I, as depicted above, wherein $R^1$ and $R^2$ are defined as above, comprising reacting a compound of the formula

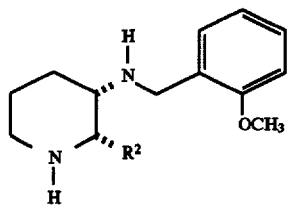

(III)

with hydrogen in the presence of a metal containing catalyst to form a compound of the formula IV, as depicted above, wherein $R^2$ is defined as above, and then converting the compound of formula IV so formed to a compound of the formula I using one of the procedures described above.

DETAILED DESCRIPTION OF THE INVENTION

The processes and products of the present invention are illustrated in the following reaction scheme. Except where otherwise indicated, in the reaction scheme and discussion that follow, formulas I, II, III and IV, and substituents $R^1$, $R^2$ and X are defined as above.

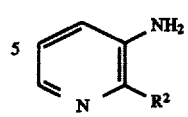

(II)

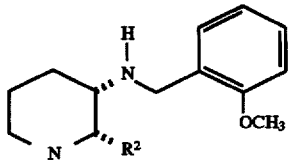

(III)

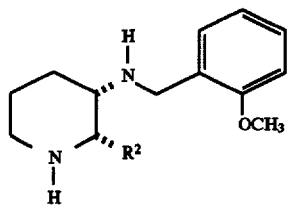

(IV)

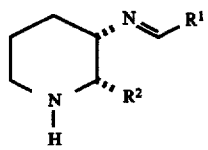

(I)

The reaction of a compound of the formula IV with a compound of the formula $R^1$CHO to produce a compound of the formula I is typically carried out in the presence of a reducing agent such as sodium cyanoborohydride, sodium triacetoxyborohydride, sodium borohydride, hydrogen and a metal catalyst, zinc and hydrochloric acid, or formic acid at a temperature from about −60° C. to about 50° C. Suitable reaction inert solvents for this reaction include lower alcohols (e.g., methanol, ethanol and isopropanol), acetic acid and tetrahydrofuran (THF). Preferably, the solvent is acetic acid, the temperature is about 25° C., and the reducing agent is sodium triacetoxyborohydride. This reaction proceeds to give material in which the addition of the $CH_2R^1$ sidechain occurs selectively at the 3-amino group, and the isomer of formula I is the only product isolated.

Alternatively, the reaction of a compound of the formula IV with a compound of the formula $R^1$CHO may be carried out in the presence of a drying agent or using an apparatus designed to remove azeotropically the water generated, to produce an imine of the formula

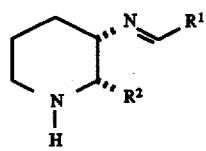

which is then reacted with a reducing agent as described above, preferably with sodium triacetoxyborohydride at about room temperature. The preparation of the imine is generally carried out in a reaction inert solvent such as benzene, xylene or toluene, preferably toluene, at a temperature from about 25° C. to about 110° C., preferably at about the reflux temperature of the solvent. Suitable drying agents/solvent systems include titanium tetrachloride/dichloromethane titanium isopropoxide/dichloromethane and molecular sieves/THF. Titanium tetrachloride/dichloromethane is preferred.

The reaction of a compound of the formula IV with a compound of the formula $R^1CH_2X$ is typically carried out in a reaction inert solvent such as dichloromethane or THF, preferably dichloromethane, at a temperature from about 0° C. to about 60° C., preferably at about 25° C.

The reaction of a compound of the formula IV with a compound of the formula

is typically carried out in an inert solvent such as tetrahydrofuran (THF) or dichloromethane at a temperature from about −20° C. to about 60° C., preferably in dichloromethane at about 0° C. Reduction of the resulting amide is accomplished by treatment with a reducing agent such as borane dimethylsulfide complex, lithium aluminum hydride or diisobutylaluminum hydride in an inert solvent such as ethyl ether or THF. The reaction temperature may range from about 0° C. to about the reflux temperature of the solvent. Preferably, the reduction is accomplished using borane dimethylsulfide complex in THF at about 60° C.

Reduction of the pyridine of formula II to form the corresponding piperidine of formula IV is generally accomplished using either sodium in alcohol, lithium aluminum hydride/aluminum trichloride, electrolytic reduction or hydrogen in the presence of a metal containing catalyst. The reduction with sodium is generally conducted in a boiling alcohol, preferably butanol, at a temperature from about 20° C. to about the reflux temperature of the solvent, preferably at about 120° C. The reduction with lithium aluminum hydride/aluminum trichloride is usually carried out in ether, THF or dimethoxyethane, preferably ether, at a temperature from about 25° C. to about 100° C., preferably at about room temperature. The electrolytic reduction is conducted, preferably, at room temperature, but temperatures from about 10° C. to about 60° C. are also suitable.

Hydrogenation in the presence of a metal containing catalyst is the preferred method of reduction. Suitable hydrogenation catalysts include palladium, platinum, nickel, platinum oxide and rhodium. The preferred catalyst for hydrogenation is platinum on carbon. The reaction temperature may range from about 10° C. to about 50° C., with about 25° C. being preferred. The hydrogenation is generally carried out at a pressure from about 1.5 to about 4 atmospheres, preferably at about 3.0 atmospheres, in a suitable inert solvent such as acetic acid or a lower alcohol, preferably methanol, with about a stoichiometric quantity of hydrogen chloride present. When the reduction is carried out via hydrogenation in the presence of a metal containing catalyst, material of the cis configuration is isolated exclusively and the pyridine ring is reduced selectively as opposed to the 2-phenyl moiety.

The preparation of compounds of the formula IV from the corresponding compounds of the formula III is accomplished, as indicated above, by treating the compounds of formula III with hydrogen in the presence of a metal containing catalyst such as platinum or palladium. Generally, this reaction is conducted in a reaction inert solvent such as acetic acid or a lower alcohol, at a temperature from about 0° C. to about 50° C. Alternatively, the compounds of formula III may be treated with a dissolving metal such as lithium or sodium in ammonia at a temperature from about −30° C. to about −78° C., or with a formate salt in the presence of palladium or with cyclohexene in the presence of palladium. Preferably, the compounds of formula III are treated with hydrogen in the presence of palladium on carbon in a mixture of methanol/ethanol in water or methanol/ethanol containing hydrochloric acid at a temperature of about 25° C. When compounds of the formula III are treated with hydrogen in the presence of a metal containing catalyst, the only products isolated are the desired compounds of the formula IV. No products derived from cleavage of the alternative benzylic position of the piperidine ring (i.e., the bond between the nitrogen at position I and the carbon at position 2) are observed.

The starting materials of the formulae

$R^1CHO$ and $R^1CH_2X$ that are used in the above reactions are either commercially available or obtainable by carrying out standard transformation well known to those skilled in the art upon commercially available materials.

In each of the above reactions wherein one piperidine derivative is converted to another piperidine derivative (i.e., III→IV and IV→I), the absolute stereochemistry about the carbons at positions 2 and 3 of the piperidine ring is preserved. Therefore, for each such reaction, a racemic mixture or a pure enantiomer may be obtained by using the appropriate starting material having the same stereochemistry.

The resolution of a racemic mixture of a compound of the formula I to prepare the (+) enantiomer of such compound is generally carried out using methanol, ethanol, or isopropanol, preferably isopropanol, as the organic reaction inert solvent. Preferably, the resolution is carried out by combining a racemic mixture of a compound of the formula I and (R)-(−)-mandelic acid in isopropanol, and stirring the mixture to form an optically enriched mandelic acid salt precipitate. The optically enriched precipitate is then recrystallized twice from isopropanol, after which the recrystallized precipitate is converted to the free base of the optically pure compound of formula I by partitioning it between dichloromethane and an aqueous base such as sodium hydroxide, sodium bicarbonate or potassium bicarbonate, preferably sodium hydroxide, or by stirring an alcoholic solution of the salt with a basic ion exchange resin. The free base, which is dissolved in the methylene chloride, can then be converted to the corresponding hydrochloric acid salt. Isolation of the mandelate may be conducted at temperatures from about 0° C. to about 40° C. About 25° C. is preferred.

In each of the reactions discussed or illustrated above, pressure is not critical unless otherwise indicated. Pressures from about 0.5 atmospheres to about 5.0 atmospheres are generally acceptable, and ambient pressure, i.e., about one atmosphere, is preferred as a matter of convenience.

The compounds of Formula I and their pharmaceutically acceptable salts exhibit substance P receptor antagonist activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P receptor antagonists for the control and/or treatment of any of the aforesaid clinical conditions in mammals, including humans.

The compounds of the formula I and the pharmaceutically acceptable salts thereof can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed.

The following examples illustrate the methods and compounds of the present invention but do not limit its scope.

As indicated above, the starting materials used in the reaction of this invention are either commercially available or obtainable by carrying out standard transformation well known to those skilled in the art upon commercially available materials. Table 1 below indicates how the aldehydes of the formula $R^1CHO$ used in the examples were obtained. The standard transformations used to prepare these aldehydes are identified by one or more lower case letters in the column labelled "Reaction Sequence" in Table 1. The letters used to identify such transformations are explained in the key following Table 1.

TABLE 1

Preparation of $R^1CHO$

| $R^1$ | Starting Material | Reaction* Sequence |
|---|---|---|
| 2,5-dimethoxyphenyl | — | commercial |
| 4,5-difluoro-2-methoxyphenyl | 3,4-difluoro-methoxybenzene | a |
| 2-chloro-5-fluorophenyl | — | commercial |
| 2-ethoxyphenyl | — | commercial |
| 2-hydroxyphenyl | — | commercial |
| 3,5-difluoro-2-methoxyphenyl | 2,4-difluoro-methoxybenzene | a |
| 2-chloro-2-fluorophenyl | — | commercial |
| 5-chloro-2-methoxyphenyl | 4-chloro-methoxybenzene | a |
| 3-fluoro-2-methoxyphenyl | 3-fluoro-2-hydroxybenzaldehyde | b |
| 5-chloro-3-fluoro-2-methoxyphenyl | 4-chloro-2-fluorophenol | b, a |
| 3-chloro-5-fluoro-2-methoxyphenyl | 2-chloro-4-fluoro-methoxybenzene | a |
| 3,5-chloro-2-methoxyphenyl | 2,4-dichloro-methoxybenzene | a |
| 4-methoxyphenyl | — | commercial |
| 2-thienyl | — | commercial |
| 2-methoxynaphthyl | — | commercial |
| 3-thienyl | — | commercial |
| 2,5-difluorophenyl | — | commercial |
| 2,4-dimethoxyphenyl | — | commercial |
| 2,4-dichloro-6-methoxyphenyl | 3,5-dichloro-methoxybenzene | a |
| 2,6-dichloro-4-methoxyphenyl | 3,5-dichloro-methoxybenzene | a |
| 3,4-dichloro-2-methoxyphenyl | 2,3-dichloro-methoxybenzene | a |
| 2,3-dimethoxyphenyl | — | commercial |
| 5-bromo-2-methoxy-3-methylphenyl | 2-methyl-methoxybenzene | c, a |
| 2-cyclopentyloxyphenyl | 2-hydroxybenzaldehyde | d |
| 2-cyclopentyloxy-5-methoxyphenyl | 2-hydroxy-5-methoxybenzaldehyde | d |
| 5-t-butyl-2-methoxyphenyl | 4-t-butylphenol | e, a |
| 5-s-buytl-2-methoxyphenyl | 4-s-butylphenol | e, a |
| 5-fluoro-2-methoxypheny | 4-fluoro-methoxybenzene | a |
| 2-acetamidophenyl | 2-aminobenzaldehyde | f |
| 2-methoxyphenyl | — | commercial |
| 5-isopropyl-2-methoxyphenyl | 4-isopropyl-methoxybenzene | a |
| 5-n-propyl-2-methoxyphenyl | 4-n-propylphenol | e, a |
| 4,5-dimethyl-2-methoxyphenyl | 3,4-dimethylphenol | e, a |
| 5-heptyl-2-methoxyphenyl | 4-heptylphenol | e, a |
| 2-heptyloxy-5-methoxyphenyl | 4-heptyloxyphenol | e, a |
| 5-heptyloxy-2-methoxyphenyl | 4-heptyloxyphenol | e, a |
| 2-(2,2,2-trifluoroethoxy)phenyl | 2-chlorobenzonitrile | g, h |
| quinolin-8-yl | 8-methylquinoline | i |
| 5-hydroxy-2-methoxyphenyl | 4-methoxyphenol | a |
| 2-methoxy-5-phenylphenyl | 4-phenylphenol | e, a |
| 4-amino-5-chloro-2-methoxyphenyl | 4-amino-5-chloro-2-methoxybenzoic acid | j |
| 2-hydroxy-5-trifluoromethoxyphenyl | 2-methoxy-5-trifluoromethoxybenzaldehyde | k |
| 5-t-butyl-2-hydroxyphenyl | 4-t-butylphenol | a |
| 3-trifluoromethoxyphenyl | — | commercial |
| 5-chloro-2-(2,2,2-trifluoroethoxy)phenyl | 2,6-dichlorobenzonitrile | g, h |

TABLE 1-continued

Preparation of R¹CHO

| R¹ | Starting Material | Reaction* Sequence |
|---|---|---|
| 5-carbomethoxy-2-methoxyphenyl | 5-carbomethoxy-2-hydroxybenzaldehyde | e |
| 5-t-butyl-2-trifluoromethoxyphenyl | trifluoromethoxybenzene | l, m |
| 5-n-butyl-2-methoxyphenyl | 4-n-butylphenol | e, a |
| 2-ethoxy-5-trifluoromethoxyphenyl | 4-trifluoromethoxyphenol | n, a |
| 2-methoxy-5-phenoxyphenyl | 4-phenoxyphenol | e, a |
| 5-ethyl-2-methoxyphenyl | 4-ethyl-methoxybenzene | a |
| 2-difluoromethoxy-5-trifluoromethoxyphenyl | 2-hydroxy-5-trifluoromethoxybenzaldehyde | p |
| 5-isopropyl-2-(2,2,2-trifluoroethoxy)phenyl | 4-isopropyl-iodobenzene | g, a |
| 2-isopropoxy-5-trifluoromethoxyphenyl | 4-trifluoromethoxyphenol | q, a |
| 5-dimethylamino-2-methoxyphenyl | 5-amino-2-hydroxybenzaldehyde | e, r |
| 5-t-butyl-2-difluoromethoxyphenyl | 4-t-butylphenol | a, p |
| 2-methoxy-5-(N-methylsulfonamido)phenyl | 5-amino-2-hydroxybenzoic acid | s |
| 5-methylmercapto-2-methoxyphenyl | 4-methylthiophenol | e, a |
| 2-methoxy-5-methylaminomethylphenyl | 2-methoxy-5-(N-methylcarboxamido)benzaldehyde | t |
| 2-methoxy-5-methylsulfoxyphenyl | 5-methylmercapto-2-methoxybenzaldehyde | u |
| 2-methoxy-5-methylsulfonylphenyl | 5-methylmercapto-2-methoxybenzaldehyde | u |
| 2,5-bis(difluoromethoxy)phenyl | 2,5-dihydroxybenzaldhyde | p |
| 2-difluoromethoxy-5-dimethylaminophenyl | 5-amino-2-hydroxybenzaldehyde | r, p |
| 2-difluoromethoxy-5-isopropylphenyl | 4-isopropylphenol | a, p |
| 2-difluoromethoxy-5-methylthiophenyl | 4-methylthiophenol | e, m, k, p |
| 2-difluoromethoxy-5-nitrophenyl | 2-hydroxy-5-nitrobenzaldehyde | p |
| 5-dimethylamino-2-(2,2,2-trifluoroethoxy)pheny | 2-chloro-5-nitrobenzonitrile | g, r, h |
| 5-acetamido-2-(2,2,2-trifluoroethoxy)phenyl | 5-nitro-2-(2,2,2-trifluoroethoxy)benzonitrile | v, f, h |
| 2-difluoromethoxy-5-ethylphenyl | 4-ethyl-methoxybenzene | a, k, p |
| 5-chloro-2-difluoromethoxyphenyl | 5-chloro-2-hydroxy-benzaldehyde | p |
| 2-trifluoromethoxyphenyl | — | commercial |
| 2-methoxy-5-trifluoromethoxyphenyl | 4-trifluoromethoxyphenol | e, a |

*Reagents for Preparation of R¹CHO From Standard Routes
a) $Cl_2CHOCH_3$, $TiCl_4$
b) dimethylsulfate
c) $Br_2$/HOAc
d) cyclopentyl bromide
e) methyl iodide
f) acetyl chloride
g) $NaOCH_2CF_3$
h) Raney nickel, $HCO_2H$
i) $SeO_2$
j) 1) carbonyldiimdazole, 2) N,O-dimethylhydroxylamine, 3) diisolbutylaluminum hydride
k) $BBr_3$
l) t-butyl chloride/$AlCl_3$
m) $Cl_2CHOCH_3$/$AlCl_3$
n) ethyl iodide
p) $ClF_2CH$
r) isopropyl bromide
r) $H_2$, Pd/C, HCHO
s) 1) methanol/HCl, 2) methylsulfonyl chloride, 3) methyl iodide, 4) diisobutylauminum hydride,
5) $MnO_2$
t) borane methylsulfide complex
u) monoperoxyphthalic acid, magnesium salt hexahydrate
v) $H_2$—Pd/$BaSO_4$

EXAMPLE 1

(+)-(2S,3S)-3-Amino-2-phenylpiperidine

In a bottle were placed 9 g of 10% palladium-carbon, 180 ml of methanol, 275 ml of ethanol, 6.5 ml of concentrated hydrochloric acid and 9 g of the hydrochloride salt of (2S,3S)-3-(2-methoxybenzylamino)-2-phenylpiperidine. The mixture was shaken under hydrogen (40 p.s.i.) overnight, 9 g of additional catalyst were added to the system and the mixture was shaken under hydrogen for 1 day. The mixture was diluted with water (250 mL), filtered through diatomaceous earth (Celite (trademark)) and the Celite was rinsed well with water. The filtrate was concentrated to a volume of ca. 600–700 mL, made basic with concentrated aqueous sodium hydroxide and extracted with chloroform, and the chloroform extracts were dried (sodium sulfate) and concentrated to obtain 4.4 g of the title compound as a colorless oil.

$[\alpha]_D$ (HCl Salt)=+62.8° (c=0.46, methanol ($CH_3OH$)).

¹H NMR (CDCl₃) δ1.68 (m, 4H), 2.72 (m, 1H), 2.94 (broad s, 1H), 3.16 (m, 1H), 3.80 (d, 1H, J=3), 7.24 (m, 5H).

HRMS Calc'd for $C_{11}H_{16}N_2$:176.1310. Found: 176.1309. Calc'd for $C_{11}H_{16}N_2.2HCl.\frac{1}{3}H_2O$: C, 51.78; H, 7.36; N, 10.98. Found: C, 51.46; H, 7.27; N, 10.77.

EXAMPLE 2

(+)-(2S,3S)-3-(2,5-Dimethoxybenzylamino)-2-phenylpiperidine

Under a nitrogen atmosphere in a round-bottom flask were placed 600 mg (3.4 mmol) of (+)-(2S,3S)-3-amino-2-phenylpiperidine, 8 ml of acetic acid and 622 mg (3.7 mmol) of 2,5-dimethoxybenzaldehyde, and the mixture was stirred for 30 minutes. To the system were added 1.58 g (7.5 mmol) of sodium triacetoxyborohydride, and the mixture was stirred at room temperature overnight. The mixture was concentrated, basified with 1M aqueous sodium hydroxide and extracted with methylene chloride. The methylene chloride extracts were washed with water and extracted with 1M aqueous hydrochloric acid. The hydrochloric acid extracts were basified with 1M aqueous sodium hydroxide and extracted with methylene chloride. The methylene chloride extracts were dried (sodium sulfate) and concentrated to obtain 528 mg of colorless oil. The oil was dissolved in methylene chloride, and ether saturated with hydrogen chloride was added to the solution. The resulting white solid was collected by filtration and stirred in isopropanol at 60° C. for 2 hours. Filtration afforded 414 mg of the title compound as its hydrochloride. Additional material (400 mg) was obtained by extracting the initial basic layer with additional methylene chloride, drying (sodium sulfate) and concentration. $[\alpha]_D$ (HCl salt)=+60.5° (c=0.58, CH₃OH).

¹H NMR (CDCl₃) δ1.38 (m, 1H), 1.58 (m, 1H) 1.88 (m, 1H), 2.13 (m, 1H), 2.78 (m, 2H), 3.25 (m, 1H), 3.36 (d, 1H, J=18), 3.44 (s, 3H), 3.62 (d, 1H, J=18), 3.72 (s, 3H), 3.88 (d, 1H, J=3), 6.62 (m, 3H), 7.24 (m, 5H).

Mass spectrum: m/z 326(parent).

Calc'd for $C_{20}H_{26}N_2O_2.2HCl.0.25H_2O$: C,59.48; H, 7.11;N, 6.93. Found: C, 59.33; H, 6.91; N, 7.23.

EXAMPLE 3

Cis-3-amino2-phenylpiperidine

In a bottle were placed 2.65 g (15.6 mmol) of 3-amino-2-phenylpyridine, 10.6 g of 5% platinum/carbon and 106 mL of 1.5 M HCl in methanol. The mixture was shaken under an atmosphere (ca. 40 p.s.i.) of hydrogen for 2.5 hours. Water was added to the system, the mixture was filtered through a pad of diatomaceous earth and the pad was rinsed with ca. 700 mL of water. The filtrate was made basic with solid sodium hydroxide and extracted with two portions of dichloromethane. The combined organic fractions were washed with water, dried (sodium sulfate) and concentrated with a rotary evaporator to obtain 2.4 g of the title compound as a yellow oil.

Calc'd for $C_{11}H_{16}N_2O.0.25H_2O$: C, 73.08; H, 9.20; N, 15.89. Found: C, 72.80; H, 9.46; N, 15.84.

The title compounds if Examples 4–23 and 25–81 were prepared from either (+)-(2S,3S)-3-amino-2-phenylpiperidine or the corresponding racemate by employing the appropriate aldehyde and using a procedure similar to that of Example 2.

EXAMPLE 4

Cis-3-(4,5-difluoro-2-methoxybenzylamino)-2-phenylpiperidine

¹H NMR (CDCl₃) δ1.30 (m, 1H), 1.62 (m, 2H), 1.96 (m, 1H), 2.68 (m, 2H), 3.18 (m, 2H), 3.32 (s, 3H), 3.44 (d, 1H, J=14), 3.82 (d, 1H, J=3), 6.38 (dd, 1H, J=6,12), 6.66 (dd, 1H, J=8, 10), 7.16 (m, 5H).

HRMS Calc'd for $C_{19}H_{22}N_2F_2O$: 332.1697. Found 332.1698. Calc'd for $C_{19}H_{22}N_2OF_2.2HCl.0.85H_2O$: C, 54.25; H, 6.15; N, 6.66. Found: C, 54.26; H, 5.84; N, 6.94.

EXAMPLE 5

Cis-3-(2-chloro-4-fluorobenzylamino)-2-phenylpiperidine

¹H NMR (CDCl₃) δ1.44 (m, 1H), 2.06 (m, 1H), 2.78 (m, 2H), 3.24 (m, 1H), 3.40 (d, 1H, J=12), 3.58 (d, 1H, J=12), 3.88 (d, 1H, J=3), 6.75 (m, 1H), 6.92 (m, 2H), 7.26 (m, 5H).

HRMS Calc'd for $C_{18}H_{20}N_2{}^{35}ClF$:318.1294. Found 318.1280.

EXAMPLE 6

Cis-3-(2-ethoxybenzylamino)-2phenylpiperidine

¹H NMR (CDCl₃) δ1.10 (t, 3H, J=5), 1.40 (m, 1H), 1.62 (m, 1H), 1.90 (m, 1H), 2.14 (m, 1H), 2.80 (m, 2H), 3.27 (m, 1H), 3.38 (d, 1H, J=15), 3.69 (m, 3H), 3.86 (d, 1H, J=2), 6.64 (d, 1H, J=8), 6.78 (t, 1H, J=6), 6.94 (d, 1H, J=6), 7.12 (t, 1H, J=8), 7.24 (m, 5H).

HRMS Calc'd for $C_{20}H_{26}N_2O$:310.2041. Found: 310.2045.

EXAMPLE 7

Cis-3-(2-hydroxybenzylamino)2-phenylpiperidine

¹H NMR (CDCl₃) δ1.62 (m, 3H), 2.10 (m, 1H), 2.79 (m, 1H), 2.92 (m, 1H), 3.20 (m, 1H), 3.48 (s, 2H), 3.82 (d, 1H, J=2), 6.72 (m, 3H), 7.08 (m, 1H), 7.36 (m, 5H).

HRMS Calc'd for $C_{18}H_{22}N_2O$:282.1732. Found: 282.1724. Calc'd for $C_{18}H_{22}N_2O.2HCl.2H_2O$: C, 55.26, H, 7.20; N, 7.16. Found: C, 55.13; H, 7.12; N, 6.84.

EXAMPLE 8

Cis-3-(3,5-difluoro2-methoxybenzylamino)-2-phenylpiperidine

¹H NMR (CDCl₃) δ1.45 (m, 1H), 1.64 (m, 1H), 1.86 (m, 1H), 2.08 (m, 1H), 2.80 (m, 2H), 3.24 (m, 1H), 3.44 (d, 1H, J=15), 3.54 (d, 1H, J=15), 3.68 (s, 3H), 3.90 (d, 1H, J=3), 6.57 (dd, 1H, J=8, 9), 6.69 (dd, 1H, J=9, 12), 7.28 (m, 5H).

HRMS Calc'd for $C_{19}H_{22}N_2OF_2$:332.1698. Found: 332.1700. Calc'd for $C_{19}H_{22}N_2OF_2.2HCl$:C, 56.30; H, 5.97; N, 6.92. Found: C, 56.17; H, 5.84; N, 6.59.

EXAMPLE 9

Cis-3-(2-chloro-6-fluorobenzylamino)-2-phenylpiperidine

¹H NMR (CDCl₃) δ1.40 (m, 1H), 1.66 (m, 1H), 1.90 (m, 1H), 2.15 (m, 1H), 2.78 (m, 2H), 3.26 (m, 1H), 3.68 (d, 2H, J=18), 3.72 (d, 1H, J=18), 6.82 (m, 1H), 7.04 (m, 2H), 7.22 (m, 5H).

HRMS Calc'd for $C_{18}H_{20}N_2ClF.2HCl.\frac{2}{3}H_2O$: C, 53.56; H, 5.83; N, 6.95. Found: C, 53.63; H, 5.53; N, 6.83.

EXAMPLE 10

(2S,3S)-3-(5-chloro-2methoxybenzylamino)-2-phenylpiperidine

Mp 275°–277° C. (HCl salt).

$^1$H NMR (CDCl$_3$) δ1.40 (m, 1H), 1.60 (m, 1H), 1.90 (m, 1H), 2.08 (m, 1H), 2.79 (m, 2H), 3.26 (m, 1H), 3.36 (d, 1H, J=15), 3.45 (s, 3H), 3.60 (d, 1H, J=15), 3.88 (d, 1H, J=3), 6.56 (d, 1H, J=8), 6.92 (d, 1H, J=3), 7.06 (dd, 1H, J=3, 8), 7.28 (m, 5H).

Mass spectrum: m/z 330 (parent).

EXAMPLE 11

Cis-3-(5-chloro-2-methoxybenzylamino)-2-phenylpiperidine $^1$H NMR (CDCl$_3$) δ1.37 (m, 1H), 1.56 (m, 1H), 1.86 (m, 1H), 2.06 (m, 1H), 2.76 (m, 2H), 3.23 (m, 1H), 3.32 (d, 1H, J=15), 3.42 (s, 3H), 3.58 (d, 1H, J=15), 3.85 (d, 1H, J=3), 6.54 (d, 1H, J=8), 6.90 (d, 1H, J=3), 7.04 (dd, 1H, J=3, 8), 7.24 (m, 5H).

EXAMPLE 12

Cis-3(2,5-dimethoxybenzylamino)-2-phenylpiperidine

M.p. 250°–252° C. (HCl salt).

$^1$H NMR (CDCl$_3$) δ1.28–1.40 (m, 1H), 1.48–1.92 (m, 2H), 2.02–2.14 (m, 1H), 2.66–2.80 (m, 2H), 3.14–3.24 (m, 1H), 3.32 (d, 1H, J=18), 3.38 (s, 3H), 3.56 (d, 1H, J=18), 3.66 (s, 3H), 3.83 (d, 1H, J=3), 6.48–6.62 (m, 3H), 7.10–7.26 (m, 5H).

HRMS Calc'd for C$_{20}$H$_{26}$N$_2$O$_2$:326.1995. Found: 326.1959. Anal. Calc'd for C$_{20}$H$_{26}$N$_2$O$_2$.2HCl.0.3H$_2$O:C, 59.34; H, 7.12; N, 6.92. Found: C, 59.33; H, 6.96; N, 6.76.

EXAMPLE 13

Cis-3-(5-fluoro-2-methoxybenzylamino)-2-phenylpiperidine

M.p. 270°–272° C. (HCl salt).

HRMS Calc'd for C$_{19}$H$_{23}$FN$_2$O:314.1791. Found: 314.1766. Anal. Calc'd for C$_{19}$H$_{23}$FN$_2$O.2HCl.0.5H$_2$O:C, 57.58; H, 6.61; N, 7.07. Found: C, 57.35; H, 6.36; N, 7.03.

$^1$H NMR (CDCl$_3$) δ1.30–1.42 (m, 1H), 1.48–2.12 (m, 3H), 2.64–2.82 (m, 2H), 3.12–3.26 (m, 1H), 3.32 (d, 1H, J=12), 3.42 (s, 3H), 3.56 (d, 1H, J=12), 3.84 (d, 1H, J=3), 6.53 (dd, 1H, J=5, 10), 6.64 (dd, 1H, J=3, 8), 6.70–6.80 (m, 1H), 7.12–7.40 (m, 5H).

EXAMPLE 14

Cis-2-phenyl-3-[2-(prop-2-yloxy)benzylamino]piperidine $^1$H NMR (CDCl$_3$) δ1.00 (m, 6H), 1.30 (m, 1H), 1.70 (m, 2H), 2.10 (m, 1H), 2.72 (m, 2H), 3.18 (m, 1H), 3.30 (m, 1H), 3.50 (m, 1H), 3.80 (br s, 1H), 4.06 (m, 1H), 6.66 (m, 2H), 6.90 (m, 1H), 7.05 (m, 1H), 7.20 (m, 5H).

HRMS Calc'd for C$_{21}$H$_{28}$N$_2$O:324.2197. Found: 324.2180. Calc'd for C$_{21}$H$_{28}$N$_2$O.2HCl.1.66H$_2$O:C, 59.02; H, 7.85; N, 6.55. Found: C, 59.07; H, 7.77; N, 6.69.

EXAMPLE 15

Cis-3-(3-fluoro-2-methoxybenzylamino)-2-phenylpiperidine $^1$H NMR (CDCl$_3$) δ1.40 (m, 1H), 1.60 (m, 1H), 1.86 (m, 1H), 2.08 (m, 1H), 2.80 (m, 2H), 3.23 (m, 1H), 3.36 (m, 1H), 3.58 (m, 4H), 3.88 (m, 1H), 6.80 (m, 3H), 7.26 (m, 5H).

HRMS Calc'd for C$_{19}$H$_{23}$FN$_2$O:314.1794. Found: 314.1768. Calc'd for C$_{19}$H$_{23}$FN$_2$O.2HCl.1.5H$_2$O:C, 55.08; H, 6.80; N, 6.76. Found: C, 54.89; H, 6.48; N, 6.79.

EXAMPLE 16

Cis-3-(5-chloro-3-fluoro-2-methoxybenzylamino)-2-phenylpiperidine $^1$H NMR (CDCl$_3$) δ1.42 (m, 1H), 1.54 (m, 1H), 1.80 (m, 1H), 2.06 (m, 1H), 2.78 (m, 2H), 3.20 (m, 1H), 3.42 (d, 1H, J=15), 3.58 (d, 1H, J=15), 3.64 (s, 3H), 3.86 (m, 1H), 6.66 (d, 1H, J=9), 6.91 (d, 1H, J=9), 7.26 (m, 5H).

HRMS Calc'd for C$_{19}$H$_{22}$FN$_2$OCl:348.1401. Found: 348.1406.

EXAMPLE 17

Cis-3-(3-chloro-5-fluoro-2-methoxybenzylamino)-2-phenylpiperidine $^1$H NMR (CDCl$_3$) δ1.44 (m, 1H), 1.58 (m, 1H), 1.80 (m, 1H), 2.06 (m, 1H), 2.80 (m, 2H), 3.22 (m, 1H), 3.42 (d, 1H, J=18), 3.54 (d, 1H, J=18), 3.66 (s, 3H), 3.88 (d, 1H, J=2), 6.55 (d, 1H, J=6), 6.92 (d, 1H, J=9), 7.26 (m, 5H).

HRMS Calc'd for C$_{19}$H$_{22}$ClFN$_2$O:348.1401. Found: 348.1411. Calc'd for C$_{19}$H$_{22}$ClFN$_2$O.2HCl.0.25H$_2$O:C, 53.53; H, 5.79; N, 6.57. Found: C, 53.58; H, 5.60; N, 6.41.

EXAMPLE 18

Cis -3-(3,5-dichloro-2-methoxybenzylamino)-2-phenylpiperidine $^1$H NMR (CDCl$_3$) δ1.44 (m, 1H), 1.56 (m, 1H), 1.82 (m, 1H), 2.08 (m, 1H), 2.80 (m, 2H), 3.20 (m, 1H), 3.50 (m, 2H), 3.64 (s, 3H), 3.88 (m, 1H), 6.68 (s, 1H), 7.26 (m, 6H).

HRMS Calc'd for C$_{19}$H$_{22}$Cl$_2$N$_2$O:364.1105. Found: 364.1105. Calc'd for C$_{19}$H$_{22}$Cl$_2$N$_2$O.2HCl:C, 52.07; H, 5.52; N, 6.39. Found: C, 51.69; H, 5.50; N, 6.32.

EXAMPLE 19

Cis-3-(4-Methoxybenzylamino)-2-phenylpiperidine

M.p. 264°–266° C. (HCl salt).

$^1$H NMR (CDCl$_3$) δ1.28–1.40 (m, 1H), 1.44–1.88 (m, 2H), 1.92–2.02 (m, 1H), 2.64–2.84 (m, 2H), 3.10–3.22 (m, 1H), 3.19 (d, 1H, J=12), 3.39 (d, 1H, J=12), 3.70 (s, 3H), 3.81 (d, 1H, J=3), 6.65 (d, 2H, J=8), 6.83 (d, 2H, J=6), 7.12–7.28 (m, 5H).

HRMS Calc'd for C$_{19}$H$_{24}$N$_2$O: 296.1885. Found: 296.1871. Calc'd for C$_{19}$H$_{24}$N$_2$O.2HCl.0.6H$_2$O: C, 60.03; H, 7.21; N, 7.37. Found: 60.08; H, 7.11; N, 7.45.

EXAMPLE 20

Cis-2-Phenyl-3-(thien-2-ylmethylamino)piperidine

M.p. 250°–252° C. (HCl salt).

$^1$H NMR (CDCl$_3$) δ1.30–1.40 (m, 1H), 1.46–1.52 (m, 1H), 1.68–1.86 (m, 1H), 1.92–2.00 (m, 1H), 2.64–2.78 (m, 1H), 2.84–2.92 (m, 1H), 3.12–3.22 (m, 1H), 3.44 (d, 1H, J=12), 3.54 (d, 1H, J=12), 3.81 (d, 1H, J=3), 6.53 (d, 1H, J=4), 6.72–6.80 (m, 1H), 7.02 (d, 1H, J=6), 7.12–7.30 (m, 5H).

HRMS Calc'd for C$_{16}$H$_{20}$N$_2$S:272.1373. Found: 272.1327. Calc'd for C$_{16}$H$_{20}$N$_2$S.2HCl.1.1H$_2$O: C, 52.62; H, 6.67; N, 7.67. Found: C, 52.64; H, 6.38; N, 7.65.

EXAMPLE 21

Cis-3 -(2-Methoxynapth-1-ylmethylamino)-2-phenylpiperidine

M.p. 222°–225° C. (HCl salt).

$^1$H NMR (CDCl$_3$) δ1.36–1.48 (m, 1H), 1.52–2.04 (m, 2H), 2.18–2.32 (m, 1H), 2.68–2.82 (m, 1H), 2.90 (d, 1H, J=3), 3.18–3.28 (m, 1H), 3.64 (s, 3H), 3.80 (d, 1H, J=12), 3.86 (d, 1H, J=4), 4.07 (d, 1H, J=12), 7.02–7.32 (m, 8H), 7.57 (d, 1H, J=8), 7.60–7.70 (m, 2H).

HRMS Calc'd for C$_{23}$H$_{26}$N$_2$O:346.2041. Found: 346.2043.

EXAMPLE 22

Cis-2-Phenyl-3-(thien-3-ylmethylamino)piperidine

M.p. 264°–267° C. (HCL salt).

$^1$H NMR (CDCl$_3$) δ1.30–1.40 (m, 1H), 1.46–1.64 (m, 1H), 1.70–1.88 (m, 1H), 1.92–2.02 (m, 1H), 2.68–2.78 (m, 1H), 2.80–2.88 (m, 1H), 3.14–3.22 (m, 1H), 3.31 (d, 1H, J=12), 3.48 (d, 1H, J=12), 3.84 (d, 1H, J=3), 6.65 (d, 1H, J=6), 6.72 (d, 1H, J=3), 7.04–7.10 (m, 1H), 7.14–7.28 (m, 5H).

HRMS Calc'd for C$_{16}$H$_{20}$N$_2$S:272.1342. Found: 272.1364. Calc'd for C$_{16}$H$_{20}$N$_2$S.2HCl.0.6H$_2$O:C, 53.96; H, 6.57; N, 7.87. Found: C, 53.97; H, 6.25; N, 7.77.

EXAMPLE 23

Cis-3-(2,5-Difluorobenzylamino)-2-phenylpiperidine

M.p. 274°–276° C. (HCL salt).

$^1$H NMR (CDCl$_3$) δ1.28–1.40 (m, 1H), 1.44–1.62 (m, 1H), 1.66–1.84 (m, 1H), 1.90–2.00 (m, 1H), 2.64–2.76 (m, 2H), 2.10–3.20 (m, 1H), 3.32 (d, 1H, J=12), 3.44 (d, 1H, J=12), 3.81 (d, 1H, J=3), 6.50–6.58 (m, 1H), 6.62–6.78 (m, 2H), 7.10–7.26 (m, 5H).

HRMS Calc'd for C$_{18}$H$_{20}$F$_2$N$_2$:302.1590. Found: 302.1560. Calc'd for C$_{18}$H$_{20}$F$_2$N$_2$.2HCl.0.2H$_2$O:C, 57.06; H, 5.96; N, 7.39. Found: C, 56.94; H, 5.94; N, 7.37.

EXAMPLE 24

(2S,3S)-3-Amino-2-phenylpiperidine

In a bottle were placed 31 g of 10% palladium-carbon, 50 mL of water, 300 mL of methanol, 450 mL of ethanol, 20 mL of concentrated aqueous hydrochloric acid and 15 g (0.04 mole) of the hydrochloride salt of (2S,3S)-3-(2-methoxybenzyl)amino-2-phenylpiperdine. The mixture was shaken under hydrogen (40 p.s.i.) for 1 day and filtered through a pad of diatomaceous earth. The pad was rinsed with 2N aqueous hydrochloric acid (HCl), water, ethanol and water and concentrated with a rotary evaporator. Water was added to the residue and the mixture was made basic using 4N aqueous sodium hydroxide (NaOH). The mixture was extracted with four portions of dichloromethane, and the extracts were dried over magnesium sulfate (MgSO$_4$) and concentrated to obtain 2.23 g of the title compound. The aqueous fraction was concentrated to dryness and triturated with chloroform. Concentration of the chloroform solution afforded an additional 4.15 g of title compound. The product obtained in this manner had spectral properties identical to those of the product of Example 1.

EXAMPLE 25

Cis-3-(2,4-dimethoxybenzyl)amino-2-phenylpiperidine $^1$H NMR (CDCl$_3$) δ1.38 (m, 1H), 1.65 (m, 1H), 1.9 (m, 2H), 2.15 (m, 1H), 2.8 (m, 2H), 3.25 (m, 1H), 3.35 (d, 1H, J=15), 3.4 (s, 3H), 3.6 (d, 1H, J=15), 3.78 (s, 3H), 3.85 (d, 1H, J=3), 6.25 (d, 1H, J=3), 6.35 (dd, 1H, J=10, 3), 6.85 (d, 1H, J=10), 7.30 (m, 5H).

Mass spectrum m/z 326 (parent).

Anal. calc'd for C$_{20}$H$_{26}$N$_2$O$_2$.2HCl:C, 60.14; H, 7.07, N, 7.02 Found: C, 59.66; H, 7.11; N, 6.83.

EXAMPLE 26

Cis-3-(2,4 dichloro-6-methoxybenzyl)amino-2-phenylpiperidine

M.p. 256°–258° C. (HCl salt).

$^1$H NMR (CDCl$^3$) δ1.4 (m, 1H), 1.62 (m, 3H), 1.94 (m, 1H), 2.2 (m, 1H), 2.68 (m, 1H), 2.76 (m, 1H), 3.2 (m, 1H), 3.38 (s, 3H), 3.4 (d, 1H, J=10), 3.64 (d, 1H, J=10), 3.84 (m, 1H), 6.48 (d, 1H, J=3), 6.84 (d, 1H, J=3), 7.2 (m, 5H).

Mass Spectrum m/z 364 (parent).

Anal. calc'd for C$_{19}$H$_{22}$Cl$_2$N$_2$O.2HCl: C, 52.07; H, 5.52; N, 6.39. Found: C, 51.81; H, 5.65; N, 6.17.

EXAMPLE 27

Cis-3-(2,6-dichloro-4-methoxybenzyl)amino-2-phenylpiperidine

M.p. 230°–240° C. (HCl salt).

$^1$H NMR (CDCl$_3$) δ1.4 (m, 1H), 1.6 (m, 3H), 1.92 (m, 1H), 2.16 (m, 1H), 2.76 (m, 2H), 3.2 (m, 1H), 3.58 (d, 1H, J=12), 3.70 (s, 3H), 3.74 (d, 1H, J=12), 3.86 (d, 1H, J=3), 6.66 (m, 2H), 7.2 (m, 5H).

Mass Spectrum m/z 364 (parent).

Anal. calc'd for C$_{19}$H$_{22}$Cl$_2$NO$_2$.2HCl: C, 52.07; H, 5.52; N, 6.39. Found: C, 52.18; H, 5.46; N, 6.24.

EXAMPLE 28

Cis-3-(3,4-dichloro-2-methoxybenzyl)amino-2-phenylpiperidine

M.p. 246°–248° (HCl salt).

$^1$H NMR (CDCl$_3$) δ1.4 (m, 1H), 1.65 (s, 2H), 1.9 (m, 1H), 2.05 (m, 2H), 2.8 (m, 2H), 3.25 (m, 1H), 3.45 (d, 1H, J=15), 3.6 (d, 1H, J=15), 3.9 (m, 4H), 6.65 (d, 1H, J=10), 6.90 (d, 1H, J=10), 7.3 (m, 5H).

HRMS Calc'd for C$_{19}$H$_{22}$Cl$_2$N$_2$O.2HCl: C, 52.07; H, 5.52; N, 6.39. Found: C, 51.58; H, 5.46; N, 6.26.

EXAMPLE 29

Cis-3-(2,3-dimethoxybenzyl)amino-2-phenylpiperidine

M.p. 238°–240° C. (HCl salt).

$^1$H NMR (CDCl$_3$) δ1.44 (m, 1H), 1.6 (m, 1H), 2.00 (m, 2H), 2.8 (dt, 2H, J=12, 3), 2.92 (m, 1H), 3.26 (m, 1H), 3.42 (d, 1H, J=10), 3.52 (s, 3H), 3.53 (d, 1H, J=10), 3.78 (s, 3H), 3.84 (m, 1H), 3.90 (d, 1H, J=3), 6.52 (d, 1H, J=10), 6.72 (d, 1H, J=10), 6.84 (d, 1H, J=10), 7.82 (m, 5M).

HRMS Calc'd for C$_{20}$H$_{26}$N$_2$O$_2$: 326.2058. Found: 326.1991.

Anal. calc'd for C$_{20}$H$_{26}$N$_2$O$_2$.2HCl½ H$_2$O: C, 58.82; H, 7.16; N, 6.86. Found C, 58.63; H, 7.26; N, 6.81.

EXAMPLE 30

Cis-3-(5-bromo-2-methoxy-3-methylbenzyl)amino-2-phenylpiperidine

M.p. 236°–238° C. (HCl salt).

$^1$H NMR (CDCl$_3$) δ1.44 (m, 1H), 1.64 (m, 1H), 1.90 (m, 1H), 2.16 (s, 3H), 2.80 (m, 2H), 3.26 (m, 1H), 3.36 (d, 1H, J=12), 3.43 (s, 1H), 3.52 (d, 1H, J=12) 3.90 (m, 1H), 6.92 (s, 1H), 7.10 (s, 1H), 7.34 (m, 5H).

HRMS calc'd for C$_{20}$H$_{25}$BrN$_2$O: 388.1144. Found: 388.1153.

EXAMPLE 31

(2S,3S)-3-(2,4-dimethoxybenzyl)amino-2-phenylpiperidine $^1$H NMR (CDCl$_3$) δ1.4 (m, 1H), 1.58 (m, 1H), 1.94 (m, 2H), 2.1 (m, 1H), 2.8 (m, 2H), 3.28 (m, 1H), 3.34 (d, 1H, J=15), 3.38 (s, 3H), 3.64 (d, 1H, J=15)), 3.76 (s, 3H), 3.88 (d, 1H, J=3), 6.24 (d, 1H, J=3), 6.30 (dd, 1H, J=10, 3), 6.86 (d, 1H, J=10), 7.26 (m, 5H).

HRMS Calc'd for C$_{20}$H$_{26}$N$_2$O$_2$: 326.1988: Found: 326.1986.

Anal. calc'd for C$_{20}$H$_{26}$N$_2$O$_2$.2HCl¼H$_2$O: C, 59.48; H, 7.11; N, 6.94. Found: C, 59.40; H, 6.96; N, 6.95.

EXAMPLE 32

(2S,3S)-3-(2-Cyclopentyloxybenzyl)amino-2-phenylpiperidine

M.p. 230°–232° C. (HCl salt).

$^1$H NMR (CDCl$_3$) δ1.75 (m, 13H), 2.14 (m, 1H), 2.80 (dt, 2H, J=12, 3), 2.90 (m, 1H), 3.28 (m, 1H), 3.36 (d, 1H, J=15), 3.60 (d, 1H, J=15), 3.88 (broad s, 1H), 4.58 (m, 1H), 6.74 (m, 2H), 6.84 (d, 1H, J=10), 7.12 (m, 1H), 7.30 (m, 5H).

HRMS calc'd for C$_{23}$H$_{40}$N$_2$O: 350.2351. Found: 350.2332.

Anal. calc'd for C$_{23}$H$_{30}$N$_2$O.2HCl.2H$_2$O: C; 60.12; H, 7.33; N, 6.10. Found C, 59.10; H, 7.19; N, 6.09.

EXAMPLE 33

(2S,3S)-3-(2-Cyclopentyloxy-5-methoxybenzyl)amino-2-phenylpiperidine

M.p. 217°–219° C. (MCl salt).

$^1$H NMR (CDCl$_3$) δ1.66 (m, 13H), 2.14 (m, 1H), 2.82 (dt, 2H, J=12, 3), 2.92 (m, 1H), 3.14 (m, 2H), 3.54 (d, 1H, J=15), 3.72 (s, 3H), 3.90 (d, 1H, J=15), 4.50 (m, 1H), 6.64 (m, 3H), 7.30 (m, 5H).

HRMS calc'd for C$_{24}$H$_{32}$N$_2$O$_2$: 380.2456. Found: 380.2457.

Anal. calc'd for C$_{24}$H$_{32}$N$_2$O$_2$.2HCl.H$_2$O: C, 60.14; H, 7.70; N, 5.94. Found C, 61.05; H, 7.67; N, 5.92.

EXAMPLE 34

(2S,3S)-3-(5-tert-Butyl-2-methoxybenzyl)amino-2-phenylpiperidine

M.p. 262°–264° C. (HCl salt).

$^1$H NMR (CDCl$_3$) δ1.22 (s, 9H), 1.38 (m, 2H), 1.90 (m, 1H), 2.14 (m, 1H), 2.80 (m, 2H), 3.26 (m, 1H), 3.36 (d, 1H, J=15), 3.44 (s, 3H), 3.62 (d, 1H, J=15), 3.86 (d, 1H, J=3), 6.60 (d, 1H, J=10), 7.00 (d, 1H, J=3), 7.12 (m, 1H), 7.26 (m, 5H).

HRMS calc'd for C$_{23}$H$_{32}$N$_2$O: 352.2507. Found: 352.2512.

Anal. calc'd for C$_{23}$H$_{32}$N$_2$O. 2HCl.0.5H$_2$O: C, 63.58; H, 8.12; N, 6.45. Found C, 63.75; H, 8.00; N, 6.42.

EXAMPLE 35

(2S,3S)-3-(5-sec-Butyl-2-methoxybenzyl)amino-2-phenylpiperidine

M.p. 260°–263° C. (HCl salt).

$^1$H NMR (CDCl$_3$) δ0.8 (2t, 3H, J=6), 1.16 (2d, 3H, J=7), 1.5 (m, 4H), 1.9 (m, 1H), 2.12 (m, 1H), 2.46 (m, 1H), 2.8 (m, 3H), 3.28 (m, 1H), 3.42 (d, 1H, J=15), 3.44 (s, 3H), 3.66 (d, 1H, J=15), 3.90 (d, 1H, J=3), 6.60 (d, 1H, J=10), 6.78 (broad s, 1H), 6.92 (d, 1H, J=10), 7.3 (m, 5H).

HRMS calc'd for C$_{23}$H$_{32}$N$_2$O: 352.2507. Found: 352.2525. Anal. calc'd for C$_{23}$H$_{32}$N$_2$O.2HCl.H$_2$O: C, 62.29; H, 8.18; N, 6.32. Found C, 62.95; H, 7.62; N, 6.61.

EXAMPLE 36

(2S,3S)-3-(5-Fluoro-2-methoxybenzylamino)-2-phenylpiperidine

M.p.>270° C. (HCl salt).

$^1$H NMR (CDCl$_3$) δ1.38 (m, 1H), 1.56 (m, 1H), 1.90 (m, 1H), 2.06 (m, 1H), 2.66 (m, 2H), 3.26 (m, 1H), 3.30 (d, 1H, J=15), 3.38 (s, 3H), 3.56 (d, 1H, J=15), 3.86 (d, 1H, J=3), 6.52 (m, 1H), 6.64 (dd, 1H, J=10, 3), 6.70 (dt, 1H, J=10, 3), 7.24 (m, 5H).

Anal. calc'd for C$_{19}$H$_{23}$FN$_2$O.5HCl.0.75H$_2$O: C, 57.57; H, 6.61; N, 7.06. Found: C, 57.83, H, 6.31; N, 7.06.

EXAMPLE 37

(2S,3S)-3-(4,5-Difluoro-2-methoxybenzyl)amino-2-phenylpiperdine $^1$H NMR (CDCl$_3$) δ1.36 (m, 1H), 1.55 (m, 1H), 1.84 (m, 1H), 2.02 (m, 1H), 2.72 (m, 2H), 3.20 (m, 1H), 3.26 (d, 1H, J=14), 3.42 (s, 3H), 3.52 (d, 1H, J=14), 3.84 (d, 1H, J=3), 6.42 (dd, 1H, J=6, 12), 6.70 (dd, 1H, J=8, 10), 7.20 (m, 5H).

Anal. calc'd for C$_{19}$H$_{22}$F$_2$N$_2$O.2HCl.0.55H$_2$O: C, 54.96; H, 6.09; N, 6.75. Found C, 54.65, H, 5.69; N, 6.74.

EXAMPLE 38

(2S,3S)-3-(2-Acetamidobenzyl)amino-2-phenylpiperidine

M.p. 187°–195° C. (HCl salt).

$^1$H NMR (CDCl$_3$) δ1.52 (m, 1H), 1.61 (s, 3H), 1.70 (m, 1H), 2.10 (m, 2H), 2.80 (m, 2H), 3.18 (m, 1H), 3.32 (d, 1H, J=16), 3.54 (d, 1H, J=16), 3.89 (d, 1H, J=3), 6.88 (m, 2H) 7.26 (m, 7H).

HRMS calc'd for C$_{20}$H$_{25}$N$_3$O:323.1997. Found: 323.1972.

EXAMPLE 39

(2S,3S)-3-(2-Methoxybenzyl)amino-2-phenylpiperidine $^1$H NMR (CDCl$_3$) δ1.36 (m, 1H), 1.54 (m, 1H), 2.0 (m, 2H), 2.78 (m, 2H), 3.23 (m, 1H), 3.36 (d, 1H, J=14), 3.41 (s, 3H), 3.63 (d, 1H, J=14), 3.83 (broad s, 1H), 6.61 (d, 1H, J=8), 6.74 (t, 1H, J=7), 6.91 (d, 1H, J=7), 7.08 (t, 1H, J=8), 7.12 (m, 5H).

EXAMPLE 40

(2S,3S)-3-(2-Methoxybenzyl)amino-2-phenylpiperidine

M.P. 257°–259° C. (dec.)

$^1$H NMR (free base; CDCl$_3$) δ1.32 (m, 1H), 1.50 (m, 1H), 1.82 (m, 1H), 2.04 (m, 1H), 2.30 (s, 3H), 2.72 (m, 2H), 3.18 (m, 1H), 3.26 (d, 1H, J=15), 3.36 (s, 3H), 3.54 (d, 1H, J=15), 3.80 (d, 1H, J=3), 6.52 (d, 1H, J=10), 6.90 (d, 1H, J=3), 7.04 (dd, 1H, J=3, 10), 7.2 (m, 5H).

HRMS calc'd for C$_{20}$H$_{26}$N$_2$OS: 342.1760. Found: 342.1770.

Anal. calc'd for C$_{20}$H$_{26}$N$_2$OS.2HCl.0.25H$_2$O: C, 57.20; H, 6.84; N, 6.67. Found: C, 57.35; H, 6,76; N, 6.61.

EXAMPLE 41

(2S,3S)-3-(2-Methoxy-5-methylsulfoxybenzylamino)-2-phenylpiperidine hydrochloride M.P. 209° C. (dec).

$^1$H NMR (free base; CDCl$_3$) δ1.40 (m, 1H), 1.56 (m, 1H), 1.90 (m, 1H), 2.10 (m, 1H), 2.59, 2.62 (2S, 3H), 2.76 (m, 2H), 3.22 (m, 1H), 3.42 (m, 1H), 3.49, 3.52 (2S, 3H), 3.66 (m, 1H), 3.86 (d, 1H, J=3), 6.76 (m, 1H), 7.24 (m, 6H), 7.46 (m, 1H).

HRMS calc'd for C$_{20}$H$_{27}$N$_2$O$_2$S(M+1): 359.1787. Found: 359.1763.

EXAMPLE 42

(2S,3S)-3-(2-Methoxy-5-methylsulfonylbenzylamino)-2-phenylpiperidine hydrochloride

M.P.>260° C.

$^1$H NMR (free base; CDCl$_3$) δ1.40 (m, 1H), 1.58 (m, 1H), 1.88 (m, 1H), 2.10 (m, 1H), 2.78 (m, 2H), 2.96 (s, 3H), 3.24 (m, 1H), 3.38 (d, 1H, J=15), 3.54 (s, 3H), 3.66 (d, 1H, J=15), 3.90 (d, 1H, J=3), 6.74 (d, 1H, J=10), 7.26 (m, 5H), 7.58 (d, 1H, J=3), 7.72 (d, 1H, J=10).

HRMS calc'd for C$_{20}$H$_{26}$N$_2$O$_3$S: 374.1658. Found: 374.1622.

EXAMPLE 43

(2S,3S)-3-(2-Methoxy5-phenoxybenzylamino)-2-phenylpiperidine hydrochloride

M.P.>250° C.

$^1$H NMR (free base; CDCl$_3$) δ1.34 (m, 1H), 1.74 (m, 2H), 2.06 (m, 1H), 2.76 (m, 2H), 3.22 (m, 1H), 3.32 (d, 1H, J=15), 3.44 (s, 3H), 3.60 (d, 1H, J=15), 3.85 (d, 1H, J=3), 6.60 (d, 1H, J=9), 6.67 (d, 1H, J=3), 6.78 (dd, 1H, J=6,9), 6.86 (d, 2H), 7.00 (t, 1H, J=6), 7.22 (m, 7H).

HRMS calc'd for C$_{25}$H$_{28}$N$_2$O$_2$: 388.2151. Found: 382.2137.

EXAMPLE 44

(2S,3S)-3-(2-Methylmethylsulfonamido-benzylamino)-2-phenylpiperidine hydrochloride $^1$H NMR (free base; CDCl$_3$) δ1.42 (m, 1H), 1.74 (m, 2H), 2.12 (m, 1H), 2.78 (m, 5H), 3.20 (s, 3H), 3.24 (m, 1H), 3.36 (d, 1H, J=15), 3.52 (s, 3H), 3.64 (d, 1H, J=15), 3.89 (d, 1H, J=3), 6.64 (d, 1H, J=9), 6.98 (d, 1H, J=3), 7.14 (dd, 1H, J=3, 9), 7.26 (m, 5H).

HRMS calc'd for C$_{21}$H$_{29}$N$_3$O$_3$S: 403.1992. Found: 403.1923.

Anal. calc'd for C$_{21}$H$_{29}$N$_3$O$_3$S.2HCl.⅓H$_2$O: C, 52.28; H, 6.61; N, 8.71. Found: C, 52.09; H, 6.63; N, 8.68.

EXAMPLE 45

(2S,3S)-3-(2,2,2-Trifluoroethoxybenzylamino)-2-phenylpiperidine hydrochloride

M.P.>275° C.

$^1$H NMR (free base; CDCl$_3$) δ1.44 (m, 1H), 1.62 (m, 1H), 1.90 (m, 1H), 2.10 (m, 1H), 2.82 (m, 2H), 3.26 (m, 1H), 3.38 (d, 1H, J=15), 3.66 (d, 1H, J=15), 3.92 (d, 1H, J=3), 4.06 (m, 2H), 6.66 (d, 1H, J=10), 6.94 (m, 2H), 7.16 (m, 1H), 7.30 (m, 5H).

HRMS calc'd for C$_{20}$H$_{24}$F$_3$N$_2$O(M+1): 365.1835. Found: 385.1908.

Anal. calc'd for C$_{20}$H$_{23}$F$_3$N$_2$O.2HCl.⅓H$_2$O: C, 54.19; H, 5.84; N, 6.32. Found: C, 54.22; H, 5.57; N, 6.42.

EXAMPLE 46

(2S,3S)-3-(5-Chloro-2-(2,2,2-trifluoroethoxy)benzylamino)-2-phenylpiperidine hydrochloride

M.P. 267°–269° C.

$^1$H NMR (free base; CDCl$_3$) δ1.40 (m, 1H), 1.60 (m, 1H), 1.82 (m, 1H), 2.02 (m, 1H), 2.76 (m, 2H), 3.20 (m, 1H), 3.28 (d, 1H, J=15), 3.52 (d, 1H, J=15), 3.84 (d, 1H, J=3), 4.00 (m, 2H), 6.54 (d, 1H, J=10), 6.92 (d, 1H, J=3), 7.04 (m, 1H), 7.24 (m, 5H).

HRMS calc'd for C$_{20}$H$_{22}$ClF$_3$N$_2$O: 398.1368. Found: 398.1352.

Anal. calc'd for C$_{20}$H$_{22}$ClF$_3$N$_2$O.2HCl: C, 50.91; H, 5.13; N, 5.94. Found: C, 50.89; H, 4.84; N, 5.93.

EXAMPLE 47

(2S,3S)-3-(3Trifluoromethoxybenzylamino)-2-phenylpiperidine hydrochloride

M.P.>275° C.

$^1$H NMR (free base; CDCl$_3$) δ1.4 (m, 1H), 1.54 (m, 1H), 1.80 (m, 1H), 1.96 (m, 1H), 2.74 (m, 2H), 3.18 (m, 1H), 3.30 (d, 1H, J=15), 3.46 (d, 1H, J=15), 3.82 (d, 1H, J=3), 6.80 (s, 1H), 6.84 (d, 1H, J=10), 6.92 (m, 1H), 7.12 (m, 1H), 7.24 (m, 5H).

HRMS calc'd for C$_{19}$H$_{21}$F$_3$N$_2$O: 350.1601. Found: 350.1609.

Anal. calc'd for C$_{19}$H$_{21}$F$_3$N$_2$O.2HCl: C, 53.91; H, 5.48; N, 6.62. Found: C, 53.84; H, 5.07; N, 6.59.

EXAMPLE 48

(2S,3S)-3-(5-t-Butyl-2trifluoromethoxybenzylamino)-2-phenylpiperidine hydrochloride

M.P. 262°–264° C.

$^1$H NMR (free Base; CDCl$_3$) δ1.20 (s, 9H), 1.40 (m, 1H), 1.52 (m, 1H), 1.84 (m, 1H), 2.06 (m, 1H), 2.80 (m, 2H), 3.22 (m, 1H), 3.38 (d, 1H, J=15), 3.58 (d, 1H, J=15), 3.86 (d, 1H, J=3), 6.98 (m, 1H), 7.12 (m, 2H), 7.26 (m, 5H).

HRMS calc'd for C$_{23}$H$_{29}$F$_3$N$_2$O: 406.2225. Found: 406.2271.

Anal. calc'd for C$_{23}$H$_{29}$F$_3$N$_2$O.2HCl.⅓H$_2$O: C, 56.92; H, 6.56; N, 5.77. Found: C, 56.99; H, 6.41; N, 6.03.

EXAMPLE 49

(2S,3S)-3-[5-Isopropyl-2-(2,2,2-trifluoroethoxy) benzylamino]-2-phenylpiperidine hydrochloride M.P.>280° C. $^1$H NMR (free base; $CDCl_3$) δ1.12 (m, 6H), 1.4 (m, 1H), 1.62 (m, 1H), 1.82 (m, 1H), 2.08 (m, 1H), 2.76 (m, 3H), 3.22 (m, 1H), 3.30 (d, 1H, J=15), 3.38 (d, 1H, J=15), 3.82 (d, 1H, J=3), 4.02 (m, 2H), 6.56 (d, 1H, J=10), 6.78 (d, 1H, J=3), 6.94 (m, 1H), 7.24 (m, 5H).

HRMS calc'd for $C_{23}H_{30}F_3N_2O$ (M+1): 407.2303. Found: 407.2287.

Anal. calc'd for $C_{23}H_{29}F_3N_2O\cdot2HCl\cdot\tfrac{1}{2}H_2O$: C, 56.55, H, 6.60; N, 5.70. Found: C, 56.17; H, 6.39; N, 5.77.

EXAMPLE 50

(2S,3S)-3-(2-Methoxy-5methylaminomethylbenzylamino)-2-phenylpiperidine hydrochloride

M.P. 242° C.

$^1$H NMR (free base; $CDCl_3$) δ1.36 (m, 1H), 1.58 (m, 1H), 1.90 (m, 1H), 2.10 (m, 1H), 2.38 (s, 3H), 2.80 (m, 2H), 3.22 (m, 1H), 3.42 (m, 4H), 3.56 (s, 2H), 3.64 (d, 1H, J=15), 3.86 (d, 1H, J=3), 6.60 (d, 1H, J=10), 6.86 (d, 1H, J=3), 7.02 (m, 1H), 7.26 (m, 5H).

HRMS calc'd for $C_{21}H_{30}N_3O$ (M+1): 340.2382. Found: 340.2400.

EXAMPLE 51

(2S,3S)-3-[5-Dimethylamino-2-(2,2,2-trifluoroethoxy)benzylamino]-2-phenylpiperidine hydrochloride.

M.P. 250°–252° C.

$^1$H NMR (free base; $CDCl_3$) δ1.40 (m, 1H), 1.60 (m, 1H), 1.86 (m, 1H), 2.10 (m, 1H), 2.82 (m, 8H), 3.22 (m, 1H), 3.34 (d, 1H, J=15), 3.58 (d, 1H, J=15), 3.88 (d, 1H, J=3), 4.00 (m, 2H), 6.42 (d, 1H, J=3), 6.50 (m, 1H), 6.64 (d, 1H, J=10), 7.30 (m, 5H).

HRMS calc'd for $C_{22}H_{28}F_3N_3O$: 407.2178. Found: 407.2179.

EXAMPLE 52

(2S,3S)-3-(2-Difluoromethoxy-5-methylmercaptobenzylamino)-2phenylpiperidine hydrochloride

M.P. 254°–256° C.

$^1$H NMR (free base; $CDCl_3$) δ1.45 (m, 1H), 1.60 (m, 1H), 1.80 (m, 1H), 2.10 (m, 1H), 2.40 (s, 3H), 2.80 (m, 2H), 3.20 (m, 1H), 3.30 (d, 1H, J=15), 3.55 (d, 1H, J=15), 3.90 (d, 1H, J=3), 6.10 (t, 1H, J=85), 6.95 (m, 3H), 7.25 (m, 5H).

HRMS calc'd for $C_{20}H_{25}Cl_2F_2N_2OS$(M+1): 379.1650. Found: 379.1668.

Anal. calc'd for $C_{20}H_{24}N_2OF_2Cl_2\cdot2HCl\cdot\tfrac{1}{4}H_2O$: C, 52.69; H, 5.86; N, 6.14. Found: C, 52.36; H, 5.86; N, 6.14.

EXAMPLE 53

(2S,3S)-3-(5-sec-Butyl-2-methoxybenzyl)amino-2-phenylpiperidine

M.P. 260°–263° C. (HCl salt).

$^1$H NMR (free base; $CDCl_3$) δ0.8 (2t, 3H, J=6), 1.16 (2d, 3H, J=7), 1.5 (m, 4H), 1.9 (m, 1H), 2.12 (m, 1H), 2.46 (m, 1H), 2.8 (m, 3H), 3.28 (m, 1H), 3.42 (d, 1H, J=15), 3.44 (s, 3H), 3.66 (d, 1H, J=15), 3.90 (d, 1H, J=3), 6.60 (d, 1H, J=10), 6.78 (broad s, 1H), 6.92 (d, 1H, J=10), 7.3 (m, 5H).

HRMS calc'd for $C_{23}H_{32}N_2O$: 352.2507. Found: 352.2525.

EXAMPLE 54

(2S,3S)-3-(4-Amino-5-chloro-2methoxybenzyl)amino2-phenylpiperidine hydrochloride M.P. 200°–203° C. (dec).

$^1$H NMR (free base; $CDCl_3$) δ1.35 (m, 1H), 1.56 (m, 1H), 1.86 (m, 1H), 2.05 (m, 1H), 2.75 (m, 2H), 3.22 (m, 2H), 3.36 (s, 3H), 3.48 (d, 1H, J=12), 3.84 (d, 1H, J=2), 6.08 (s, 1H), 6.78 (s, 1H), 7.24 (m, 5H).

HRMS calc'd for $C_{19}H_{24}ClN_3O$: 345.1604. Found: 345.1589.

EXAMPLE 55

(2S,3S)-3-(2-Methoxy-5-phenylbenzylamino)-2-phenylpiperidine hydrochloride

M.P. 238°–339° C. (dec).

$^1$H NMR (free base; $CDCl_3$) δ1.38 (m, 1H), 1.60 (m, 1H), 1.88 (m, 1H), 2.12 (m, 1H), 2.80 (m, 2H), 3.23 (m, 1H), 3.45 (m, 4H), 3.70 (d, 1H, J=12), 3.86 (d, 1H, J=3), 6.70 (d, 1H, J=6), 7.34 (m, 12H).

HRMS calc'd for $C_{25}H_{28}N_2O$: 372.2197. Found: 372.2172.

EXAMPLE 56

(2S,3S)-2-Phenyl-3-(quinolin-8-yl)methylpiperidine hydrochloride

M.P. 252°–253° C. (dec).

$^1$H NMR (free base; $CDCl_3$) δ1.38 (m, 1H), 1.58 (m, 1H), 1.94 (m, 1H), 2.17 (m, 1H), 2.78 (m, 2H), 3.24 (m, 1H), 3.83 (d, 1H, J=3), 3.96 (d, 1H, J=15), 4.28 (d, 1H, J=15), 7.14 (m, 6H), 7.32 (m, 2H), 7.58 (t, 1H, J=4), 7.98 (d, 1H, J=6), 8.46 (m, 1H).

HRMS calc'd for $C_{21}H_{23}N_3$: 317.1887. Found: 317.1883.

EXAMPLE 57

(2S,3S)-3-(5-Heptyloxy-2methoxybenzyl)amino-2-phenylpiperidine hydrochloride

M.P. 230° C. (dec).

$^1$H NMR (free base; $CDCl_3$) δ0.90 (m, 2H), 1.38 (m, 10H), 1.76 (m, 4H), 2.12 (m, 1H), 2.80 (m, 2H), 3.26 (m, 1H), 3.38 (d, 1H, J=16), 3.42 (s, 3H), 3.62 (d, 1H, J=15), 3.82 (t, 2H, J=6), 3.88 (d, 1H, J=3), 6.62 (m, 3H), 7.28 (m, 5H).

HRMS calc'd for $C_{26}H_{38}N_2O_2$: 410.2928. Found: 410.2953.

EXAMPLE 58

(2S,3S)-3-(2-Heptyloxy-5methoxybenzyl)amino-2-phenylpiperidine hydrochloride

M.P. 212°–213° C. (dec).

$^1$H NMR (free base; $CDCl_3$) δ0.90 (m, 3H), 1.60 (m, 13H), 2.12 (m, 1H), 2.80 (m, 2H), 3.26 (m, 1H), 3.36 (d, 1H, J=15), 3.62 (m, 6H), 3.86 (d, 1H, J=3), 6.60 (m, 3H), 7.23 (m, 5H).

EXAMPLE 59

(2S,3S)-3-(5-Heptyl-2-methoxybenzyl)amino-2-phenylpiperidine hydrochloride

M.P. 242°–243° C. (dec).

$^1$H NMR (free base; CDCl$_3$) δ0.88 (m, 3H), 1.60 (m, 13H), 2.14 (m, 1H), 2.44 (t, 2H, J=6), 2.78 (m, 2H), 3.26 (m, 1H), 3.40 (m, 4H), 3.64 (d, 1H, J=15), 3.86 (d, 1H, J=2), 6.58 (d, 1H, J=6), 6.75 (d, 1H, J=2), 6.92 (d, 1H, J=6), 7.26 (m, 5H).

HRMS calc'd for C$_{26}$H$_{38}$N$_2$O: 394.2977. Found: 394.3009.

EXAMPLE 60

(2S,3S)-3-(2-Methoxy-5-n-propylbenzyl)amino-2-phenylpiperidine hydrochloride

M.P. 245°–247° C. (dec).

$^1$H NMR (free base; CDCl$_3$) δ0.9 (t, 3H, J=10), 1.4 (m, 1H), 1.54 (m, 2H), 1.92 (m, 1H), 2.14 (m, 1H), 2.44 (t, 2H, J=6), 2.80 (m, 2H), 3.26 (s, 1H), 3.40 (d, 1H, J=15), 3.44 (s, 3H), 3.66 (d, 1H, J=15), 3.90 (s, 1H), 6.56 (d, 1H, J=10), 6.76 (s, 1H), 6.92 (d, 1H, J=10), 7.26 (m, 5H).

HRMS calc'd for C$_{22}$H$_{30}$N$_2$O: 338.2351. Found: 338.2339.

Anal. calc'd for C$_{22}$H$_{30}$N$_2$O.2HCl.0.25 H$_2$O: C, 63.57, H, 7.81; N, 6.74. Found: C, 63.59; H, 7.66; N, 6.73.

EXAMPLE 61

(2S,3)-3-(4,5-Dimethyl-2-methoxybenzyl)amino-2-phenylpiperidine hydrochloride

M.P. 269°–270° C.

$^1$H NMR (free base; CDCl$_3$) δ1.40 (m, 1H), 1.60 (m, 1H), 1.96 (m, 2H), 2.14 (s, 3H), 2.18 (s, 3H), 2.80 (m, 2H), 3.30 (m, 1H), 3.40 (d, 1H, J=15), 3.42 (s, 3H), 3.62 (d, 1H, J=15), 3.90 (d, 1H, J=3), 6.48 (s, 1H), 6.70 (s, 1H), 7.28 (m, 5H).

HRMS calc'd for C$_{21}$H$_{28}$N$_2$O: 324.2195. Found: 324.2210.

Anal. calc'd for C$_{21}$H$_{28}$N$_2$O.2HCl.0.25H$_2$O: C, 62.80; H, 7.60; N, 6.99. Found: C, 62.64; H, 7.31; N, 6.86.

EXAMPLE 62

(2S,3S)-3-(5-t-Butyl-2-hydroxybenzyl)amino-2-phenylpiperidine hydrochloride

M.P. 267°–269° C. (dec).

$^1$H NMR (free base; CDCl$_3$) δ1.3 (s, 9H), 1.6 (m, 3H), 2.18 (m, 1H), 2.82 (m, 1H), 2.98 (m, 1H), 3.22 (m, 1H), 3.44 (d, 1H, J=15), 3.56 (d, 1H, J=15), 3.92 (m, 1H), 6.70 (m, 2H), 7.14 (m, 1H), 7.40 (m, 5H).

HRMS Calc'd for C$_{22}$H$_{30}$N$_2$O: 338.2351. Found: 338.2384.

EXAMPLE 63

(2S,3S)-3-(5-Carbomethoxy-2-methoxybenzyl)amino-2-phenylpiperidine hydrochloride

M.P. 238°–240° C.

$^1$H NMR (free base; CDCl$_3$) δ1.4 (m, 1H), 1.6 (m, 1H), 1.88 (m, 1H), 2.1 (m, 1H), 2.75 (m, 2H), 3.2 (m, 1H), 3.35 (d, 1H, J=15), 3.45 (s, 3H), 3.7 (d, 1H, J=15), 3.85 (m, 4H), 6.65 (d, 1H, J=10), 7.2 (m, 5H), 7.70 (d, 1H, J=3), 7.85 (m, 1H).

HRMS calc'd for C$_{21}$H$_{26}$N$_2$O$_3$: 354.1937. Found: 354.1932.

EXAMPLE 64

(2S,3S)-3-(5-n-Butyl-2-methoxybenzyl)amino-2-phenylpiperidine hydrochloride

M.P. 252°–253° C.

$^1$H NMR (free base; CDCl$_3$) δ0.88 (t, 3H, J=10), 1.38 (m, 3H), 1.56 (m, 3H), 1.96 (m, 2H), 2.18 (m, 1H), 2.50 (t, 2H, J=10), 2.86 (m, 2H), 3.30 (m, 1H), 3.44 (d, 1M, J=15), 3.48 (s, 3H), 3.68 (d, 1H, J=15), 3.82 (d, 1H, J=3), 6.62 (d, 1H, J=10), 6.80 (s, 1H), 6.86 (d, 1H, J=10), 7.3 (m, 5H).

HRMS calc'd for C$_{23}$H$_{32}$N$_2$O: 352.2507. Found: 352.2509.

Anal. calc'd for C$_{23}$H$_{32}$N$_2$O.2HCl.⅓H$_2$O: C, 64.03; H, 8.09; N, 6.50. Found: C, 64.39; H, 7.90; N, 6.59.

EXAMPLE 65

(2S,3S)-3-(5-Isopropyl-2-methoxybenzyl)amino-2-phenylpiperidine hydrochloride

M.P. 252°–254° C.

$^1$H NMR (free base; CDCl$_3$) δ1.14 (d, 6H, J=6), 1.36 (m, 1H), 1.58 (m, 1H), 1.88 (m, 1H), 2.1 (m, 1H), 2.76 (m, 3H), 3.24 (m, 1H), 3.36 (d, 1H, J=15), 3.42 (s, 3H), 3.60 (d, 1H, J=15), 3.86 (d, 1H, J=3), 6.56 (d, 1H, J=10), 6.80 (d, 1H, J=3), 6.84 (m, 1H), 7.24 (m, 5H).

HRMS calc'd for C$_{22}$H$_{30}$N$_2$O: 338.2351. Found: 338.2377.

Anal. calc'd for C$_{22}$H$_{30}$N$_2$O.2HCl.¼H$_2$O: C, 63.52; H, 7.88; N, 6.74. Found: C, 63.33; H, 7.64; N, 6.75.

EXAMPLE 66

(2S,3S)-3-(2-Difluoromethoxy-5-N,N-dimethylaminobenzylamino)-2-phenylpiperidine hydrochloride M.P. 243°–245° C. (dec).

$^1$H NMR (free base; CDCl$_3$) δ1.44 (m, 1H), 1.72 (m, 2H), 2.10 (m, 1H), 2.84 (m, 8M), 3.21 (m, 1H), 3.28 (d, 1H, J=15), 3.55 (d, 1H, J=15), 3.88 (d, 1H, J=3), 6.08 (t, 1H, J=72), 6.36 (d, 1H, J=3), 6.46 (dd, 1H, J=3,9), 6.86 (d, 1H, J=9), 7.28 (m, 5H).

HRMS calc'd for C$_{21}$H$_{27}$F$_2$N$_3$O: 375.2122. Found: 375.2138.

Anal. calc'd for C$_{21}$H$_{27}$F$_2$N$_3$O.3HCl.½H$_2$O: C, 51.07; H, 6.44; N, 8.51. Found: C, 50.71; H, 6.08; N, 8.28.

EXAMPLE 67

(2S,3S)-3-[2,5[bis-(difluoromethoxy)benzyl)amino]-2-phenylpiperidine hydrochloride

M.P. 238°–239° C.

$^1$H NMR (free base; CDCl$_3$) δ1.64 (m, 3H), 2.04 (m, 1H), 2.76 (m, 2H), 3.18 (m, 1H), 3.28 (d, 1H, J=12), 3.52 (d, 1H, J=12), 3.84 (d, 1H, J=3), 6.12 (t, 1H, J=75), 6.40 (t, 1H, J=75), 6.75 (m, 2H), 6.94 (d, 1H, J=9), 7.24 (m, 5H).

HRMS calc'd for C$_{20}$H$_{22}$F$_4$N$_2$O$_2$: 398.1612. Found: 398.1591.

EXAMPLE 68

(2S,3S)-3-(5-t-Butyl-2-difluoromethoxybenzylamino)-2-phenylpiperidine hydrochloride M.P. 263°–264° C. (dec).

$^1$H NMR (free base; CDCl$_3$) δ1.24 (s, 9H), 1.42 (m, 1H), 1.62 (m, 1H), 1.80 (m, 1H), 2.10 (m, 1H), 2.80 (m, 2H), 3.24 (m, 2H), 3.58 (d, 1H, J=12), 3.87 (brs, 1H), 6.18 (t, 1H, J=72), 6.86 (d, 1H, J=6), 7.00 (brs, 1H), 7.12 (m, 1H), 7.24 (m, 5H).

HRMS calc'd for C$_{23}$H$_{30}$F$_2$N$_2$O: 388.2321. Found: 388.2336.

EXAMPLE 69

(2S,3S)-3-(5Dimethylamino-2-methoxybenzylamino)-2-phenylpiperidine hydrochloride

M.P.>275° C.

$^1$H NMR (free base; CDCl$_3$) δ1.34 (m, 1H), 1.70 (m, 2H), 2.10 (m, 1H), 2.76 (m, 8H), 3.20 (m, 1H), 3.34 (m, 4H), 3.56 (d, 1H, J=12), 3.82 (d, 1H, J=2), 6.50 (m, 3H), 7.22 (m, 5H).

HRMS calc'd for C$_{21}$H$_{29}$N$_3$O: 339.2306. Found: 339.2274.

Anal. calc'd for C$_{21}$H$_{29}$N$_3$O .3HCl.H$_2$O: C, 54.02; H, 7.34; N, 9.00. Found: C, 53.84; H, 7.55; N, 8.92.

EXAMPLE 70

(2S,3S)-3-(2-Isopropoxy-5-trifluoromethoxybenzylamino)-2-phenylpiperidine hydrochloride M.P. 245°–246° C. (dec).

$^1$H NMR (free base: CDCl$_3$) δ1.08 (d, 3H, J=6), 1.12 (d, 3H, J=6), 1.40 (m, 1H), 1.64 (m, 1H), 1.87 (m, 1H), 2.08 (m, 1H), 2.78 (m, 2H), 3.02 (m, 1H), 3.34 (d, 1H, J=15), 3.51 (d, 1H, J=15), 3.85 (d, 1H, J=2), 4.28 (m, 1H), 6.01 (d, 1H, J=9), 6.82 (m, 1H), 6.91 (m, 1H), 7.24 (m, 5H).

HRMS calc'd for C$_{22}$H$_{27}$F$_3$N$_2$O$_2$: 408.2024. Found: 408.2019.

Anal. calc'd for C$_{22}$H$_{27}$F$_3$N$_2$O$_2$.2HCl: C, 54.89; H, 6.07, N, 5.82. Found: C, 54.50; H, 6.24; N, 5.78.

EXAMPLE 71

(2S,3S)-3-(2-Difluoromethoxy-5-trifluoromethoxybenzylamino)-2-phenylpiperidine hydrochloride M.P. 257°–259° C. (dec).

$^1$H NMR (free base; CDCl$_3$) δ1.44 (m, 1H), 1.58 (m, 1H), 1.78 (m, 1H), 2.03 (m, 1H), 2.78 (m, 2H), 3.20 (m, 1H), 3.32 (d, 1H, J=15), 3.54 (d, 1H, J=15), 3.87 (d, 1H, J=2), 6.15 (t, 1H, J=72), 6.94 (m, 3H), 7.26 (m, 5H).

HRMS calc'd for C$_{20}$H$_{21}$F$_5$N$_2$O$_2$: 416.1523. Found: 416.1501.

Anal. calc'd for C$_{20}$H$_{21}$F$_5$N$_2$O$_2$.2HCl.⅓H$_2$O: C, 48.50; H, 4.81; N, 5.65. Found: C, 48.45; H, 4.57; N, 5.66.

EXAMPLE 72

(2S,3S)-3-(2-Ethoxy-5-trifluoromethoxybenzylamino)-2-phenylpiperidine hydrochloride M.P.>275° C. (dec).

$^1$H NMR (free base; CDCl$_3$) δ1.13 (t, 3H, J=6), 1.38 (m, 1H), 1.70 (m, 2H), 2.06 (m, 1H), 2.74 (m, 2H), 3.22 (m, 1H), 3.30 (d, 1H, J=15), 3.68 (m, 3H), 3.84 (br s, 1H), 6.55 (d, 1H, J=9), 6.79 (br s, 1H), 6.90 (m, 1H), 7.2 (m, 5H).

HRMS calc'd for C$_{21}$H$_{25}$F$_3$N$_2$O$_2$: 394.1868. Found: 394.1875.

Anal. calc'd for C$_{21}$H$_{25}$F$_3$N$_2$O$_2$.2HCl: C, 53.97; H, 5.82; N, 6.00. Found: C, 53.85; H, 5.79; N, 5.95.

EXAMPLE 73

(2S,3S)-3-(5-Ethyl-2-methoxybenzylamino)-2-phenylpiperidine hydrochloride $^1$H NMR (free base, CDCl$_3$) δ1.16 (t, 3H, J=9), 1.36 (m, 1H), 1.57 (m, 1H), 1.88 (m, 1H), 2.12 (m, 1H), 2.48 (q, 2H), 2.76 (m, 2H), 3.24 (m, 1H), 3.38 (m, 4H), 3.60 (d, 1H, J=12), 3.86 (d, 1H, J=3), 6.57 (d, 1H, J=6), 6.74 (d, 1H, J=3), 6.92 (dd, 1H, J=3,6), 7.24 (m, 5H).

HRMS calc'd for C$_{21}$H$_{28}$N$_2$O: 324.2202. Found: 324.2202.

EXAMPLE 74

(2S,3S)-3-(2-Difluoromethoxy-5-nitrobenzylamino)-2-phenylpiperidine hydrochloride $^1$H NMR (free base; CDCl$_3$) δ1.50 (m, 1H), 1.66 (m, 1H), 1.98 (m, 2H), 2.82 (m, 2H), 3.28 (m, 1H), 3.42 (d, 1H, J=15), 3.64 (d, 1H, J=15), 3.95 (d, 1H, J=2), 6.30 (t, 1H, J=72), 7.08 (d, 1H, J=8), 7.30 (m, 5H), 8.04 (m, 2H).

FAB HRMS calc'd for C$_{19}$H$_{21}$F$_2$N$_3$O$_3$(M+1): 378.1629. Found: 378.1597.

EXAMPLE 75

(2S,3S)-3-(2-Difluoromethoxy-5-isopropylbenzylamino)-2-phenylpiperidine hydrochloride M.P. 245°–247° C. (dec).

$^1$H NMR (free base; CDCl$_3$) δ1.19 (2d, 6H, J=7), 1.50 (m, 1H), 1.75 (m, 2H), 2.12 (m, 1H), 2.83 (m, 3H), 3.25 (m, 1H), 3.35 (d, 1H, J=14), 3.60 (d, 1H, J=14), 3.90 (d, 1H, J=3), 6.20 (t, 1H, J=75), 6.90 (m, 2H), 7.00 (m, 1H), 7.30 (m, 5H).

HRMS calc'd for C$_{22}$H$_{28}$F$_2$N$_2$O: 374.2170. Found: 374.2207.

Anal. calc'd for C$_{22}$H$_{28}$F$_2$N$_2$O.2HCl.⅓H$_2$O: C, 58.28; H, 6.67; N, 6.18. Found: C, 58.17; H, 6.52; N, 6.17.

EXAMPLE 76

(2S,3S)-3-(2-Methoxy-5-hydroxybenzylamino)-2-phenylpiperidine hydrochloride

M.P. 239°–240° C. (dec).

$^1$H NMR (free base; CDCl$_3$) δ1.42 (m, 1H), 1.64 (m, 1H), 1.90 (m, 1H), 2.16 (m, 1H), 2.82 (m, 2H), 3.26 (m, 1H), 3.36 (d, 1H, J=15), 3.42 (s, 3H), 3.58 (d, 1H, J=15), 3.92 (d, 1H, J=2), 6.37 (d, 1H, J=2), 6.52 (m, 2H), 7.26 (m, 5H).

HRMS calc'd for C$_{19}$H$_{24}$N$_2$O$_2$: 312.1836. Found: 312.1865.

EXAMPLE 77

(2S,3S)-3-(2-Methoxy-5-trifluoromethoxybenzyl)-amino-2-phenylpiperidine hydrochloride M.p.>250° C.

$^1$H NMR (free base, CDCl$_3$) δ1.36 (s, 1H), 1.54 (m, 1H), 1.86 (m, 1H), 2.06 (m, 1H), 2.76 (m, 2H), 3.22 (m, 1H), 3.32 (d, 1H, J=15), 3.48 (s, 3H), 3.58 (d, 1H, J=15), 3.85 (d, 1H, J=3), 6.57 (d, 1H, J=9), 6.80 (d, 1H, J=3), 6.92 (dd, 1H, J=3, 9), 7.22 (m, 5H).

HRMS calc'd for C$_{20}$H$_{23}$F$_3$N$_2$O$_2$: 380.1711. Found: 380.1704.

Anal. calc'd for C$_{20}$H$_{23}$F$_3$N$_2$O$_2$.2HCl.0.2H$_2$O: C 52.57, H 5.60, N 6.13. Found: C 52.58, H 5.40, N 5.97.

EXAMPLE 78

(2S,3S)-3-(2-Hydroxy-5-trifluoromethoxybenzylamino)-2-phenylpiperidine hydrochloride $^1$H NMR (free base; CDCl$_3$) δ1.60 (m, 3H), 2.04 (m, 1H), 2.76 (m, 1H), 2.88 (m, 1H), 3.18 (m, 1H), 3.42 (s, 2H), 3.90 (m, 1H), 6.52 (m, 1H), 6.64 (d, 1H, J=9), 6.89 (m, 1H), 7.30 (m, 5H).

HRMS calc'd for C$_{19}$H$_{21}$F$_3$N$_2$O$_2$: 366.1545. Found: 366.1562.

Anal. calc'd for C$_{19}$H$_{21}$F$_3$N$_2$O$_2$.2HCl.½H$_2$O: C, 51.25; H, 4.90; N, 6.29. Found: C, 51.30; H, 4.75; N, 6.22.

EXAMPLE 79

(2S,3S)-3-[5-Acetamido-2-(2,2,2-trifluoroethoxy)benzylamino]-2-phenylpiperidine hydrochloride

M.P.>270° C.

$^1$H NMR (free base; CDCl$_3$) δ1.46 (m, 1H), 1.82 (m, 1H), 2.08 (m, 1H), 2.12 (s, 3H), 2.76 (m, 2H), 3.20 (m, 1H), 3.48 (d, 1H, J=15), 3.58 (d, 1H, J=15), 3.82 (m, 1H), 4.08 (m, 2H), 6.44 (m, 1H), 6.58 (d, 1H, J=10), 6.78 (m, 1H), 7.26 (m, 5H), 7.58 (m, 1H).

EXAMPLE 80

(2S,3S)-3-(2-Difluoromethoxy-5-ethylbenzylamino)-2-phenylpiperidine hydrochloride

M.P. 254°–255° C.

$^1$H NMR (free base; CDCl$_3$) δ1.12 (t, 3H, J=10), 1.36 (m, 1H), 1.44 (m, 1H), 1.82 (m, 1H), 2.10 (m, 1H), 2.48 (q, 2H, J=10), 2.8 (m, 1H), 3.10 (m, 1H), 3.34 (d, 1H, J=15), 3.58 (d, 1H, J=15), 3.9 (d, 1H, J=3), 6.12 (t, 1H, J=85), 6.78 (s, 1H), 6.90 (m, 2H), 7.28 (m, 5H).

Anal. calc'd for C$_{21}$H$_{26}$F$_2$N$_2$O.2HCl: C, 58.19; H, 6.51; N, 6.47. Found: C, 57.90; H, 6.52; N, 6.64.

EXAMPLE 81

(2S,3S)-3-(5-Chloro-2-difluoromethoxybenzylamino)-2-phenylpiperidine hydrochloride

M.P. 272°–274° C.

$^1$H NMR (free base; CDCl$_3$) δ1.48 (m, 1H), 1.64 (m, 1H), 1.84 (m, 1H), 2.08 (m, 1H), 2.84 (m, 2H), 3.24 (m, 1H), 3.34 (d, 1H, J=15), 3.56 (d, 1H, J=15), 3.90 (d, 1H, J=3), 6.12 (t, 1H, J=70), 6.90 (d, 1H, J=10), 7.02 (m, 1H), 7.12 (m, 1H), 7.3 (m, 5H).

Anal. calc'd for C$_{19}$H$_{21}$ClF$_2$N$_2$O.2HCl.½H$_2$O: C, 51.20; H, 5.33; N, 6.29. Found: C, 51.03, H, 5.32. N, 6.30.

EXAMPLE 82

(2S,3S)-Phenyl-3-(2-trifluoromethoxybenzyl)aminophenylpiperidine hydrochloride

M.p. 231°–233° C.

$^1$H NMR (free base, CDCl$_3$) δ1.40 (m, 1H), 1.60 (m, 1H), 1.84 (m, 1H), 2.05 (m, 1H), 2.78 (m, 2H), 3.22 (m, 1H), 3.42 (d, 1H, J=15), 3.56 (d, 1H, J=15), 3.86 (d, 1H, J=3), 7.08 (m, 4H), 7.24 (m, 5H). Mass spectrum: m/z 350 (parent).

Anal. calc'd for C$_{19}$H$_{21}$F$_3$N$_2$O.2HCl.0.25H$_2$O: C 53.34, H 5.54, N 6.54. Found: C 53.19, H 5.40, N 6.54.

I claim:

1. A process for preparing a compound of the formula

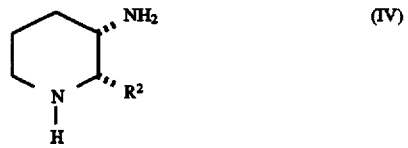

wherein R$^2$ is thienyl, benzhydryl, naphthyl or phenyl optionally substituted with from one to three substituents independently selected from chloro, bromo, fluoro, iodo, cycloalkoxy having 3 to 7 carbon atoms, (C$_1$–C$_{10}$)alkyl optionally substituted with one or more halo groups, (C$_1$–C$_{10}$)alkoxy and trifluoromethyl, comprising a selective reduction via hydrogenation in the presence of a metal containing catalyst of the compound of the formula

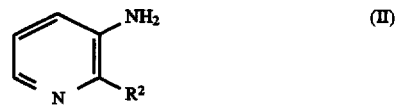

wherein R$^2$ is as defined above.

2. A process according to claim 1, wherein the selective reduction is carried out using sodium in a boiling alcohol.

3. A process according to claim 1, wherein the selective reduction is carried out using lithium aluminum hydride/aluminum trichloride.

4. A process according to claim 1, wherein the selective reduction is an electrolytic reduction.

5. A process according to claim 1, wherein the selective reduction is carried out using hydrogen in the presence of a metal containing catalyst.

6. A process according to claim 1, wherein the metal containing catalyst is selected from the group consisting of palladium, palladium on carbon, platinum, nickel, platinium oxide and rhodium.

7. A process for preparing a compound of high enantiomeric purity of the formula

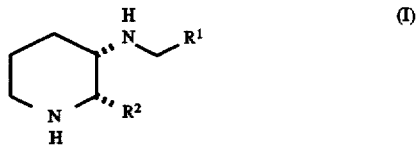

wherein R$^1$ is aryl selected from indanyl, phenyl and naphthyl; heteroaryl selected from thienyl, furyl, pyridyl and quinolyl; and cycloalkyl having 3 to 7 carbon atoms, wherein one of said carbon atoms may optionally be replaced by nitrogen, oxygen or sulfur; wherein each of said aryl and heteroaryl groups may optionally be substituted with one or more substituents, and said $(C_3-C_7)$cycloalkyl may optionally be substituted with one or two substituents, said substituents being independently selected from chloro, fluoro, bromo, iodo, nitro, $(C_1-C_{10})$alkyl optionally substituted with from one to three fluoro groups, $(C_1-C_{10})$alkoxy optionally substituted with from one to three fluoro groups, amino, $(C_1-C_{10})$alkyl-S—,

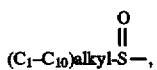

$(C_1-C_{10})$alkyl-SO$_2$—, phenyl, phenoxy, $(C_1-C_{10})$alkyl-SO$_2$NH—, $(C_1-C_{10})$alkyl-SO$_2$NH—$(C_1-C_{10})$alkyl—, $(C_1-C_{10})$alkylamino-di$(C_1-C_{10})$alkyl—, cyano, hydroxyl, cycloalkoxy having 3 to 7 carbon atoms, $(C_1-C_6)$alkylamino, $(C_1-C_6)$dialkylamino,

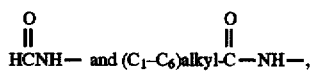

wherein the nitrogen atoms of said amino and $(C_1-C_6)$ alkylamino groups may optionally be protected with an appropriate protecting group; and $R^2$ is thienyl, benzhydryl, naphthyl or phenyl optionally substituted with from one to three substituents independently selected from chloro, bromo, fluoro, iodo, cycloalkoxy having 3 to 7 carbon atoms, $(C_1-C_{10})$alkyl optionally substituted with from one to three fluoro groups and $(C_1-C_{10})$alkoxy optionally substituted with from one to three fluoro groups, comprising reacting a compound of the formula

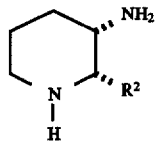 (IV)

wherein $R^2$ is defined as above, with either (a) a compound of the formula

R$^1$CX, wherein $R^1$ is defined as above and X is a leaving group, followed by treatment of the resulting amide with a reducing agent, (b) a compound of the formula R$^1$CHO, wherein $R^1$ is defined as above, in the presence of a reducing agent, or (c) a compound of the formula R$^1$CH$_2$X, wherein $R^1$ is defined as above and X is a leaving group.

8. A process according to claim 7, wherein said compound of the formula IV is reacted with said compound of the formula R$^1$CHO in the presence of a reducing agent.

9. A process according to claim 8, wherein said reducing agent is sodium triacetoxyborohydride.

10. A process according to claim 8, wherein said reducing agent is sodium cyanoborohydride.

11. A process according to claim 8, wherein said reaction is conducted in a lower alcohol solvent at a temperature from about −60° C. to about 50° C.

12. A process according to claim 8, wherein said reaction is conducted in an acetic acid solvent at a temperature from about −60° C. to about 50° C.

13. A process for preparing a compound of the formula

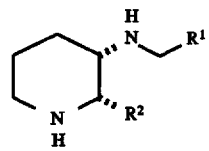 (I)

wherein $R^1$ is aryl selected from indanyl, phenyl and naphthyl; heteroaryl selected from thienyl, furyl, pyridyl and quinolyl; and cycloalkyl having 3 to 7 carbon atoms, wherein one of said carbon atoms may optionally be replaced by nitrogen, oxygen or sulfur; wherein each of said aryl and heteroaryl groups may optionally be substituted with one or more substituents, and said $(C_3-C_7)$cycloalkyl may optionally be substituted with one or two substituents, said substituents being independently selected from chloro, fluoro, bromo, iodo, nitro, $(C_1-C_{10})$alkyl optionally substituted with from one to three fluoro groups, $(C_1-C_{10})$alkoxy optionally substituted with from one to three fluoro groups, amino, $(C_1-C_{10})$alkyl-S—,

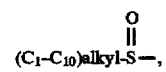

$(C_1-C_{10})$alkyl-SO$_2$—, phenyl, phenoxy, $(C_1-C_{10})$alkyl-SO$_2$NH—, $(C_1-C_{10})$alkyl-SO$_2$NH—$(C_1-C_{10})$alkyl—, $(C_1-C_{10})$alkylamino-di$(C_1-C_{10})$alkyl—, cyano, hydroxyl, cycloalkoxy having 3 to 7 carbon atoms, $(C_1-C_6)$ alkylamino, $(C_1-C_6)$dialkylamino,

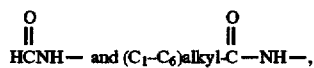

wherein the nitrogen atoms of said amino and $(C_1-C_6)$ alkylamino groups may optionally be protected with an appropriate protecting group; and $R^2$ is thienyl, benzhydryl, naphthyl or phenyl substituted with from one to three substituents independently selected from chloro, bromo, fluoro, iodo, cycloalkoxy having 3 to 7 carbon atoms, $(C_1-C_{10})$alkyl optionally substituted with from one to three groups and $(C_1-C_{10})$alkoxy optionally substituted with from one to three fluoro groups;

comprising reacting a compound of the formula

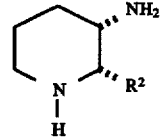 (IV)

wherein $R^2$ is defined as above, with a compound of the formula R$^1$CHO, wherein $R^1$ is defined as above, in the presence of a drying agent or using an apparatus designed to remove azeotropically the water generated, to produce an imine of the formula

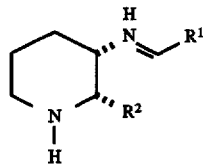

wherein $R_1$ and $R_2$ are defined as above, and reacting the imine with a reducing agent.

14. A process according to claim 13, wherein the reducing agent is sodium triacetoxyborohydride.

15. A process according to claim 7, wherein said compound of formula I formed thereby is a compound wherein $R^1$ and $R^2$ are the same or different and each of $R^1$ and $R^2$ is phenyl optionally substituted with one or more substituents independently selected from chlorine, fluorine, $(C_1-C_6)$alkyl optionally substituted with from one to three fluoro groups and $(C_1-C_6)$alkoxy optionally substituted with from one to three fluoro groups.

16. A process according to claim 7, wherein said compound of formula I formed thereby is a compound wherein $R^1$ is 2-methoxyphenyl and $R^2$ is phenyl.

17. A process according to claim 13, wherein said compound of formula I formed thereby is a compound wherein $R^1$ and $R^2$ are the same or different and each of $R^1$ and $R^2$ is phenyl optionally substituted with one or more substituents independently selected from chlorine, fluorine, $(C_1-C_6)$alkyl optionally substituted with from one to three fluoro groups and $(C_1-C_6)$alkoxy optionally substituted with from one to three fluoro groups.

18. A process according to claim 13, wherein said compound of formula I formed thereby is a compound wherein $R^1$ is 2-methoxyphenyl and $R^2$ is phenyl.

19. A process according to claim 7, wherein said compound of formula I formed thereby is a compound wherein $R^1$ is 4,5-difluoro-2-methoxyphenyl and $R^2$ is phenyl.

20. A process according to claim 13, wherein said compound of formula I formed thereby is a compound wherein $R^1$ is 4,5-difluoro-2-methoxyphenyl and $R^2$ is phenyl.

21. A process according to claim 7, wherein said compound of formula I formed thereby is a compound wherein $R^1$ is 2-methoxy-5-trifluoromethylphenyl and $R^2$ is phenyl.

22. A process according to claim 13, wherein said compound of formula I formed thereby is a compound wherein $R^1$ is 2-methoxy-5-trifluoromethylphenyl and $R^2$ is phenyl.

23. A process according to claim 7, wherein said compound of formula I formed thereby is a compound wherein $R^1$ is 2,4-dimethoxyphenyl and $R^2$ is phenyl.

24. A process according to claim 13, wherein said compound of formula I formed thereby is a compound wherein $R^1$ is 2,4-dimethoxyphenyl and $R^2$ is phenyl.

25. A process according to claim 7, wherein said compound of formula I formed thereby is a compound wherein $R^1$ is 2,3-dimethoxyphenyl and $R^2$ is phenyl.

26. A process according to claim 13, wherein said compound of formula I formed thereby is a compound wherein $R^1$ is 2,3-dimethoxyphenyl and $R^2$ is phenyl.

27. A process according to claim 7, wherein said compound of formula I formed thereby is a compound wherein $R^1$ is "5-chloro-2-methoxyphenyl" and $R^2$ is phenyl.

28. A process according to claim 13, wherein said compound of formula I formed thereby is a compound wherein $R^1$ is "5-chloro-2-methoxyphenyl" and $R^2$ is phenyl.

29. A process according to claim 7, wherein said compound of formula I formed thereby is a compound wherein $R^1$ is "3-chloro-2-methoxyphenyl" and $R^2$ is phenyl.

30. A process according to claim 13, wherein said compound of formula I formed thereby is a compound wherein $R^1$ is "3-chloro-2-methoxyphenyl" and $R^2$ is phenyl.

* * * * *

UNITED STATES PATENT AND TRADEMARK OFFICE
CERTIFICATE OF CORRECTION

PATENT NO : 5,686,615

DATED : November 11, 1997

INVENTOR(S) : Terry J. Rosen

It is certified that error appears in the above-identified patent and that said Letters Patent are hereby corrected as shown below:

Column 30, line 42 should read "fluro groups and ($C_1$ to $C_{10}$) alkoxy optionally substituted with from"

Signed and Sealed this

Fifteenth Day of May, 2001

*Attest:*

NICHOLAS P. GODICI

*Attesting Officer*     Acting Director of the United States Patent and Trademark Office